US011324705B2

(12) United States Patent
Lakhani et al.

(10) Patent No.: US 11,324,705 B2
(45) Date of Patent: May 10, 2022

(54) TRANSDERMAL DRUG DELIVERY SYSTEM

(71) Applicant: Avro Life Sciences, Inc., Kitchener (CA)

(72) Inventors: Shakir Lakhani, Richmond Hill (CA); Keean Sarani, Richmond Hill (CA)

(73) Assignee: Avro Life Sciences, Inc., Kitchener (CA)

( * ) Notice: Subject to any disclaimer, the term of this patent is extended or adjusted under 35 U.S.C. 154(b) by 0 days.

(21) Appl. No.: 16/742,842

(22) Filed: Jan. 14, 2020

(65) Prior Publication Data

US 2020/0155475 A1  May 21, 2020

Related U.S. Application Data

(63) Continuation of application No. 16/090,593, filed as application No. PCT/US2018/023073 on Mar. 19, 2018, now Pat. No. 10,576,043.

(Continued)

(51) Int. Cl.
*A61K 9/70* (2006.01)
*A61K 31/138* (2006.01)
(Continued)

(52) U.S. Cl.
CPC .......... *A61K 9/7069* (2013.01); *A61K 9/7053* (2013.01); *A61K 31/138* (2013.01); *A61K 31/343* (2013.01); *A61K 31/4409* (2013.01); *A61K 31/4545* (2013.01); *A61K 31/495* (2013.01); *A61K 31/496* (2013.01)

(58) Field of Classification Search
CPC ... A61K 9/7038; A61K 9/7046; A61K 9/7053
See application file for complete search history.

(56) References Cited

U.S. PATENT DOCUMENTS 6,010,715 A * 1/2000 Wick ................... A61K 9/7084
424/448
2006/0235048 A1* 10/2006 Weidner ............... A61K 9/0014
514/317

(Continued)

FOREIGN PATENT DOCUMENTS

CN   101559202 A  * 10/2009
CN   101559202 A    10/2009
(Continued)

OTHER PUBLICATIONS

Shidhaye et al. Mucoadhesive Bilayered Patches for Administration of Sumatriptan Succinate. AAPS PharmSciTech, vol. 9, No. 3, Sep. 2008 pp. 909-916 (Year: 2008).*

(Continued)

*Primary Examiner* — Cachet I Proctor
(74) *Attorney, Agent, or Firm* — Cognition IP, P.C.; Edward Steakley

(57) ABSTRACT

Provided herein is a water- and sweat-resistant transdermal drug delivery system for application to the skin of a mammal that comprises a patch having a diameter between 1 and 8 cm in length and a surface area between 4 and 8 cm². Also provided are methods of producing the transdermal drug delivery system and methods of treatment comprising the use of the transdermal drug delivery system.

14 Claims, 7 Drawing Sheets

Related U.S. Application Data

(60) Provisional application No. 62/543,580, filed on Aug. 10, 2017.

(51) Int. Cl.
*A61K 31/343* (2006.01)
*A61K 31/4409* (2006.01)
*A61K 31/4545* (2006.01)
*A61K 31/495* (2006.01)
*A61K 31/496* (2006.01)

(56) References Cited

U.S. PATENT DOCUMENTS

| | | | |
|---|---|---|---|
| 2007/0077282 A1* | 4/2007 | Shirai | A61K 9/7038 424/448 |
| 2007/0190124 A1* | 8/2007 | Zhang | A61L 15/44 424/448 |
| 2007/0196457 A1 | 8/2007 | Zhang et al. | |
| 2007/0259029 A1 | 11/2007 | McEntire et al. | |
| 2009/0317451 A1 | 12/2009 | Hauser | |
| 2011/0245783 A1 | 10/2011 | Stinchcomb et al. | |
| 2012/0295893 A1* | 11/2012 | Peled | A61K 31/55 514/220 |
| 2013/0144226 A1* | 6/2013 | Takada | A61K 47/02 604/307 |
| 2016/0129164 A1 | 5/2016 | Lee et al. | |
| 2017/0049712 A1* | 2/2017 | Bhalani | A61K 31/196 |
| 2017/0333410 A1* | 11/2017 | Babul | A61K 47/08 |

FOREIGN PATENT DOCUMENTS

| | | | |
|---|---|---|---|
| CN | 103 127 036 A | 6/2013 | |
| JP | 2016-504359 A | 2/2016 | |
| KR | 2013 0046842 A | 5/2013 | |
| KR | 20130046842 A * | 5/2013 | |
| WO | 2005/074883 A1 | 8/2005 | |
| WO | WO-2005074883 A1 * | 8/2005 | ........... A61K 9/0034 |
| WO | 2014/105480 A1 | 7/2014 | |

OTHER PUBLICATIONS

Furtado et al. Development of Chitosan Based Bioadhesive Bilayered Patches of Metoprolol Tartarate. International Journal of Pharmaceutical Sciences Reviewand Research. vol. 4, Issue 3, Sep.-Oct. 2010; Article 032. pp. 198-202 (Year: 2010).*

International Search Report and Written Opinion of the International Search Authority, Application No. PCT/US18/23073, dated Jul. 26, 2018.

Deshmane et al. Chitosan Based Sustained Release Mucoadhesive Buccal Patches Containing Verapamil HCL. International Journal of Pharmacy and Pharmaceutical Sciences, vol. 1, Suppl 1, Nov.-Dec. 2009 (Year: 2009).

Furtado et al. Development of Chitosan based Bioadhesive Bi layered Patches of Metoprolol tartarte International Journal of Pharmaceutical Sciences Review and Research. vol. 4, Issue 3, (Year: 2010).

Extended European Search Report in Application No. 18844305.5, dated Jul. 15, 2020.

Supriya S. Shidhaye et al., "Mucoadhesive Bilayered Patches for Administration of Sumatriptan Succinate," AAPS Pharmscitech, vol. 9, No. 3, Sep. 1, 2008, pp. 909-916, XP55710857.

* cited by examiner

TRANSDERMAL DRUG DELIVERY SYSTEM

CROSS-REFERENCE TO RELATED APPLICATIONS

This application is a continuation of U.S. application Ser. No. 16/090,593, filed on Oct. 2, 2018, which is a 35 U.S.C. § 371 national stage application of PCT International Application No. PCT/US2018/023073, filed on Mar. 19, 2018, which claims the benefit of U.S. Provisional Application No. 62/543,580, filed on Aug. 10, 2017, all of which are hereby incorporated by reference in their entirety.

FIELD

Provided herein are water- and sweat-resistant transdermal drug delivery systems for application to the skin of a mammal, that are not skin-irritating and are particularly suitable for use in subjects with sensitive skin. The disclosed transdermal delivery systems comprise a patch having a small size to allow delivery of large amounts of active agents, while minimizing the surface area of skin required for administration, a quick onset of action, sustainable drug delivery for 8-24 hours, and adhesive strength. Also provided are methods of making the disclosed transdermal drug delivery systems, and methods of using the transdermal delivery systems to treat allergic reactions, disorders of the immune system and cardiovascular diseases.

BACKGROUND

Transdermal drug delivery represents an attractive alternative to oral administration, especially where extended and consistent delivery is desired, and where the replacement of oral tablets and pills is necessary to ensure patient compliance, such as in pediatric and elderly populations.

Transdermal drug delivery provides the advantage of bypassing liver metabolism of drugs, which presents a challenge with the oral administration of drugs. In addition, transdermal drug delivery is pain-free and non-invasive, can be self-administered and provides release for long periods of time. However, only a limited number of drugs are amenable to transdermal administration. While current transdermal delivery devices may successfully deliver lipophilic small molecule drugs, it remains difficult to transdermally deliver hydrophilic drugs through the skin and into the bloodstream. Therefore, a need exists for transdermal delivery drug systems that can sustainably deliver lipophilic, hydrophilic and amphiphilic drugs, are quick to act and do not irritate the skin.

SUMMARY

It is shown herein that large molecule and small molecule drugs may be successfully delivered transdermally into the bloodstream. Based on these findings, a water- and sweat-resistant transdermal drug delivery system for application to the skin of a mammal is provided. The water-and sweat-resistant transdermal drug delivery system comprises a patch having a diameter between 1 and 8 cm in length and a surface area between 4 and 8 cm$^2$. The patch comprises a monolithic layer of about 1 to 5 mm in width, wherein the monolithic layer comprises 10-30% (w/w) of a bioadhesive polymer; 10-40% (w/w) of a film-forming agent; 10-60% (w/w) of a plasticizer; 1-20% (w/w) of a naturally occurring polysaccharide; 10-50% (w/w) of a keratolytic agent; and 1-60% (w/w) of one or more active agents. The patch has an onset of action within 15 minutes of application to the skin of a mammal, and it sustainably delivers on or more active agents for 8-24 hours. The patch has excellent adhesive strength, as shown by a peel rate of about 320 mm/min.

In some examples, the bioadhesive polymer may include chitosan, hydroxypropylmethyl cellulose, hydroxyethyl cellulose, xanthan gum, guar gum, sodium alginate, or a combination thereof. In some examples, the film-forming agent may include polyvinyl alcohol, polyvinyl pyrrolidone, carrageenan, gelatin, dextrin, polyethylene oxide, guar gum, xanthan gum, or a combination thereof. In some additional examples, the plasticizer may include glycerol, sorbitol, polyethylene glycol, polypropylene glycol, polyethylenepropylene glycol, or a combination thereof. In some other examples, the naturally occurring polysaccharide may include agar, alginate, chitin, glucomannan, gellan gum, gelatin, gum guar, gum Arabic, locust bean gum, pectin, xanthan, or a combination thereof. In some examples, the keratolytic agent may include urea, lactic acid, allantoin, benzoyl peroxide, salicyclic acid, or a combination thereof. Thus, in one example, the monolithic layer may comprise 10-30% (w/w) chitosan; 10-40% (w/w) polyvinylpyrrolidone; 10-60% glycerol; 1-20% (w/w) gum Arabic; and 10-50% (w/w) lactic acid.

In some examples, the water- and sweat-resistant transdermal drug delivery system provided herein may further comprise circular adhesive backing layer. Suitable materials for the backing layer include, but are not limited to, Teflon, metal foils, metalized polyfoils, composite foils or films containing polyester, such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. Additionally, the backing layer may include various foams, such as, but not limited to, polyolefin foams, polyvinyl chloride foams, polyurethane foams, and polyethylene foams.

The water- and sweat-resistant transdermal drug delivery system provided herein may deliver a great variety of active agents into the skin. In some example, only one active agent at the time is delivered into the skin. In other examples, a combination of active agents is delivered into the skin, either sequentially or contemporaneously. Examples of active agents include, but are not limited to, one or more antihistamines, potassium channel blockers, analgesic agents, antidiabetic agents, pain-relief agents, antidepressant agents, antipsychotic agents, anti-Parkinsonian agents, vasodilators, diuretics, calcium channel blockers, anti-acne agents, anti-aging agents, antibiotic agents, antifungal agents, ACE inhibitors, GERD medications, anti-inflammatory agents, opioids, anti-asthma agents, corticosteroids, nicotinic cholinergic receptor agonists, anti-oxidant agents, antiprotozoal agents, antipruritic agents, antiviral agents, chemotherapeutic agents, immunomodulatory agents, keratolytic agents, retinoids, and central nervous system stimulants.

Exemplary antihistamines include, but are not limited to, Diphenhydramine, Loratadine, Desloratadine, and Cetirizine. Exemplary antidepressants and anti-anxiety agents include, but are not limited to, Sertraline, Fluoxetine, Paroxetine, Venlaxafine, Duloxetine, Escitalopram Oxalate, Alprazolam, and Lorazepam. Exemplary ADHD medications include, but are not limited to, amphetamine aspartate, dextroamphetamine, methylphenidate hydrochloride, dexmethylphenidate hydrochloride, and amitriptyline. Exemplary Anti-Parkinson's medications include, but are not limited to, Levodopa, Carbidopa, Ropinirole, Pramipexole, Rotigotine, Apomorphine, Selegine Hydrochloride, Rasagiline, and Benztropine. Exemplary Multiple Sclerosis Medications include, but are not limited to, Teriflunomide, Dalfampridine, Dimethyl Fumarate, Natalizumab, Fingolimod, and Glatiramer Acetate. Exemplary Alzheimer's Medications include, but are not limited to, Donezepil, Rivastigmine, and Galantamine. Exemplary analgesics include, but are not limited to, Methadone, Hydromorphone, Oxymorphone, Buprenorphine, Hydrocodone, Morphine, and Hydrocodone. Exemplary GERD medications include, but are not limited to, esomeprazole, omeprazole, and pantoprazole. Exemplary anti-cholesterol agents include, but are not limited to, ondansentron, pioglitazone, orlistat, lenalidomide, sofusbovir, rosuvastatin, amlodipine, simvastatin, and metformin.

In some examples, the active agent is one or more of diphenhydramine, Desloratadine, Cetirizine, Loratadine, Trihexyphenidyl, Asenapine, Prostacyclin, Buspirone, Butorphanol, Captopril, Carbidopa, Albuterol, Naltrexone, Ivabradine, Dexamethasone, Phenylephrine, Fluocinolone acetonide, Dexlansoprazole, Furosemide, Isradipine, Venlafaxine, and Enalapril.

Also provided herein is a water- and sweat-resistant transdermal drug delivery system that comprises a patch that is occlusive to one or more molecules. These molecules include, but are not limited to, caffeine, aripiprazole, theophylline, dyphilline, pentoxifyline, enprofylline, aminophylline, oxtriphylline, theobromine, propentofylline, xanthinol, doxofylline, pamabrom, lisofylline, ganciclovir, fenethylline, xanthine, uric acid, rolofylline, reproterol, cafedrine and theodrenaline, and any combination thereof.

The water- and sweat-resistant transdermal drug delivery system provided herein presents several attractive features and desirable properties that make it suitable for use in a variety of mammal subject subpopulations, such as human subpopulations. For example, all components of the patch are not irritating to the skin and cause no rash, redness, inflammation or discoloration of the skin, making the water- and sweat-resistant transdermal drug delivery system particularly suitable to the elderly and pediatric populations, who tend to have sensitive skin.

In addition, because of the small size of the patch, the water- and sweat-resistant transdermal drug delivery system provided herein enables large surface-to-volume ratio to deliver large amounts of drugs and minimize the surface area of the skin required for administration, has an onset of action within 5 to 15 minutes, and allows about 65% to about 100% of one or more drugs to diffuse into the skin of a mammal within 8 to 24 hours. Thus, the water- and sweat-resistant transdermal drug delivery system provided herein provides a dosage form that achieves quick delivery through the skin into the bloodstream, reduces common side effects and improves patient compliance.

Also provided herein is a method of making a water- and sweat-resistant transdermal drug delivery system. The method comprises first adding a film-forming agent and a plasticizer to water and stirring the mixture at room temperature (25° C.); gradually adding a bioadhesive polymer and a naturally occurring polysaccharide and stir the mixture until the bioadhesive polymer is dissolved and viscosity is reduced; then adding a film-forming agent and a keratolytic agent and stirring for 2-5 hours until an even mixture is obtained; adding one or more active agents and stirring the mixture for 1-4 hours to obtain a formulation; and optionally casting the formulation onto an array of backing layers and baking the backing layers at 80° C. for 4-8 hour.

In some examples, the bioadhesive polymer may include chitosan, hydroxypropylmethyl cellulose, hydroxyethyl cellulose, xanthan gum, guar gum, sodium alginate, or a combination thereof. In some examples, the film-forming agent may include polyvinyl alcohol, polyvinyl pyrrolidone, carrageenan, gelatin, dextrin, polyethylene oxide, guar gum, xanthan gum, or a combination thereof. In some additional examples, the plasticizer may include glycerol, sorbitol, polyethylene glycol, polypropylene glycol, polyethylene-propylene glycol, or a combination thereof. In some examples, the naturally occurring polysaccharide may include agar, alginate, chitin, glucomannan, gellan gum, gelatin, gum guar, gum Arabic, locust bean gum, pectin, xanthan, or a combination thereof. In some examples, the keratolytic agent may include urea, lactic acid, allantoin, benzoyl peroxide, salicyclic acid, or a combination thereof. In one example, the patch may comprise 10-30% (w/w) chitosan; 10-40% (w/w) polyvinylpyrrolidone; 10-60% glycerol; 1-20% (w/w) gum Arabic; and 10-50% (w/w) lactic acid.

In some examples, the patch may comprise a backing layer. Suitable materials for the backing layer include, but are not limited to, Teflon, metal foils, metalized polyfoils, composite foils or films containing polyester, such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. Additionally, the backing layer may include various foams, such as, but not limited to, polyolefin foams, polyvinyl chloride foams, polyurethane foams, and polyethylene foams.

In some examples, the provided method may further comprise adding 2-15% (w/w) of one or more fatty acids. The fatty acids include, but are not limited to, tartaric acid, oleic acid, lauric acid, maleic acid, and any combination thereof. In some examples, the provided method may further comprise adding 2-15% (w/w) of one or more essential oils. Essential oils include, but are not limited to, L-menthol, chuanxiong oil, clove oil, cinnamon oil, turpentine oil, eucalyptus oil, and any combination thereof.

The provided method produces a water- and sweat-resistant transdermal drug delivery system that may deliver a great variety of active agents into the skin. In some example, only one active agent at the time is delivered into the skin. In other examples, a combination of active agents is delivered into the skin, either sequentially or contemporaneously. Examples of active agents include, but are not limited to, one or more antihistamines, potassium channel blockers, analgesic agents, antidiabetic agents, pain-relief agents, antidepressant agents, antipsychotic agents, anti-Parkinsonian agents, vasodilators, diuretics, calcium channel blockers, anti-acne agents, anti-aging agents, antibiotic agents, antifungal agents, ACE inhibitors, GERD medications, anti-inflammatory agents, opioids, anti-asthma agents, corticosteroids, nicotinic cholinergic receptor agonists, anti-oxidant agents, antiprotozoal agents, antipruritic agents, antiviral agents, chemotherapeutic agents, immunomodulatory agents, keratolytic agents, retinoids, and central nervous system stimulants.

Exemplary antihistamines include, but are not limited to, Diphenhydramine, Loratadine, Desloratadine, and Cetirizine. Exemplary antidepressants and anti-anxiety agents include, but are not limited to, Sertraline, Fluoxetine, Paroxetine, Venlaxafine, Duloxetine, Escitalopram Oxalate, Alprazolam, and Lorazepam. Exemplary ADHD medications include, but are not limited to, amphetamine aspartate, dextroamphetamine, methylphenidate hydrochloride, dexmethylphenidate hydrochloride, and amitriptyline. Exemplary Anti-Parkinson's medications include, but are not limited to, Levodopa, Carbidopa, Ropinirole, Pramipexole, Rotigotine, Apomorphine, Selegine Hydrochloride, Rasagiline, and Benztropine. Exemplary Multiple Sclerosis Medications include, but are not limited to, Teriflunomide, Dalfampridine, Dimethyl Fumarate, Natalizumab, Fingolimod, and Glatiramer Acetate. Exemplary Alzheimer's Medications include, but are not limited to, Donezepil, Rivastigmine, and Galantamine. Exemplary analgesics include, but are not limited to, Methadone, Hydromorphone, Oxymorphone, Buprenorphine, Hydrocodone, Morphine, and Hydrocodone. Exemplary GERD medications include, but are not limited to, esomeprazole, omeprazole, and pantoprazole. Exemplary anti-cholesterol agents include, but are not limited to, ondansentron, pioglitazone, orlistat, lenalidomide, sofusbovir, rosuvastatin, amlodipine, simvastatin, and metformin.

In some examples, the active agent is on or more of Diphenhydramine, Desloratadine, Cetirizine, Loratadine, Trihexyphenidyl, Asenapine, Prostacyclin, Buspirone, Butorphanol, Captopril, Carbidopa, Albuterol, Naltrexone, Ivabradine, Dexamethasone, Phenylephrine, Fluocinolone acetonide, Dexlansoprazole, Furosemide, Isradipine, Venlafaxine, and Enalapril.

The method provided herein may additionally produce a water- and sweat-resistant transdermal drug delivery system that comprises a patch that is occlusive to one or more molecules. These molecules include, but are not limited to, caffeine, aripiprazole, theophylline, dyphilline, pentoxifyline, enprofylline, aminophylline, oxtriphylline, theobromine, propentofylline, xanthinol, doxofylline, pamabrom, lisofylline, ganciclovir, fenethylline, xanthine, uric acid, rolofylline, reproterol, cafedrine and theodrenaline, and any combination thereof.

The method provided herein produces a water- and sweat-resistant transdermal drug delivery system that has an onset of action within 15 minutes of application to the skin of a mammal, and it sustainably delivers on or more active agents for 8-24 hours. The patch within the transdermal delivery system produced by the provided method has excellent adhesive strength, as shown by a peel rate of about 320 mm/min, and allows diffusion of 65% to 100% of the active agent into the skin of a mammal within 8 to 24 hours. The mammal can be an animal or a human subject.

Also provided herein is a method of treating seasonal allergic rhinitis in a subject in need thereof, wherein the method comprises applying the water- and sweat-resistant transdermal drug delivery system comprising one or more antihistamines to the subject's skin, and maintaining the water- and sweat-resistant transdermal drug delivery system in contact with the skin of the subject for 8-24 hours, thereby treating seasonal allergic rhinitis in the subject. Exemplary antihistamines include, but are not limited to, diphenhydramine, desloratidine, cetirizine, loratadine, and any combinations thereof. In some examples, the release rate of the one or more antihistamines from the patch is 600 µg/cm$^2$/hour during the first hour of applying the patch. In some examples, the release rate of the one or more antihistamines from the patch is at least 100 µg/cm$^2$/hour during the entire time of applying the patch.

Also provided herein is a method of treating seasonal chronic idiopathic urticaria in a subject in need thereof, wherein the method comprises applying the water- and sweat-resistant transdermal drug delivery system provided herein and comprising one or more antihistamines to the subject's skin, and maintaining the water- and sweat-resistant transdermal drug delivery system in contact with the skin of the subject for 8-24 hours, thereby treating seasonal chronic idiopathic urticaria in the subject. Exemplary antihistamines include, but are not limited to, diphenhydramine, desloratidine, cetirizine, loratadine, and any combinations thereof. In some examples, the release rate of the one or more antihistamines from the patch is 600 µg/cm$^2$/hour during the first hour of applying the patch. In some examples, the release rate of the one or more antihistamines from the patch is at least 100 µg/cm$^2$/hour during the entire time of applying the patch.

Also provided herein is a water- and sweat-resistant transdermal drug delivery system, wherein the patch is a monolithic layer comprising 10-30% (w/w) chitosan; 10-40% (w/w) polyvinylpyrrolidone; 10-60% glycerol; 1-20% (w/w) gum Arabic; 10-50% (w/w) lactic acid, and a therapeutically effective amount of one or more antihistamines. Exemplary antihistamines include, but are not limited to, diphenhydramine, desloratidine, cetirizine, loratadine, and any combinations thereof. In some examples, the release rate of the one or more antihistamines from the patch is 600 µg/cm$^2$/hour during the first hour of applying the patch. In some examples, the release rate of the one or more antihistamines from the patch is at least 100 µg/cm$^2$/hour during the entire time of applying the patch. In some examples, the monolithic layer may further comprise 2-15% (w/w) of one or more fatty acids. The fatty acids include, but are not limited to, tartaric acid, oleic acid, lauric acid, maleic acid, and any combination thereof. In some examples, the monolithic layer may further comprise 2-15% (w/w) of one or more essential oils. Essential oils include, but are not limited to, L-menthol, chuanxiong oil, clove oil, cinnamon oil, turpentine oil, eucalyptus oil, and any combination thereof.

The foregoing and other features of the disclosure will become more apparent from the following detailed description of several embodiments, which proceeds with reference to the accompanying figures.

DETAILED DESCRIPTION

Figure 1:
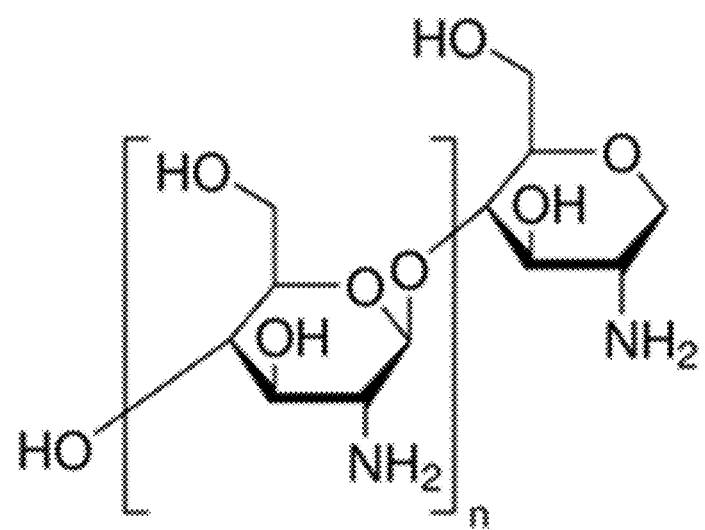
FIG. 1 shows the structure of chitosan.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

To facilitate review of the various embodiments of this disclosure, the following explanations of specific terms are provided:

Administer: To provide or give a subject an active agent, such as an antihistamine, by an effective route. Administration can be systemic or local. Exemplary routes of administration include, but are not limited to, topical, transdermal, buccal, vaginal, intranasal, rectal, inhalation, ocular, otic, enteral (e.g., oral, sublingual, buccal, rectal) and parenteral (e.g., injections (such as subcutaneous, intramuscular, intradermal, intraperitoneal, intratumoral, and intravenous) routes.

Air-Liquid Interface (ALI): A culture of cells in which the basal surface of the cells is in contact with liquid culture medium, whereas the apical surface is exposed to air. A common approach is to seed cells onto the permeable membrane of a cell culture insert, which is initially supplied with culture medium to both the apical and basal compartments. Once confluence is reached, the cells are subjected to 'air-lift', where the medium is supplied only to the basal chamber. This configuration mimics the conditions found in the human airway on the skin.

Analgesic: A drug or a group of drugs used to provide relief from pain. Analgesic drugs act in various ways on the peripheral and central nervous systems, and are distinct from anesthetics, which reversibly eliminate sensation.

Analog: A compound having a structure similar to another, but differing from it, for example, in one or more atoms, functional groups, or substructure.

Anesthetic agent: An active agent that causes reduction or loss of sensation.

Anti-Acne Agent: A chemical and/or biological agent that when topically administered at the site of acne, leads to a visible reduction of symptoms associated with the epithelial condition of acne vulgaris.

Anti-Aging Agent: A substance that treats or reduces at least an aging sign of the skin, improves skin appearance, increases thickness of one or more layers of the skin, improves skin elasticity, resiliency or firmness, improves skin hydration or moisturization, conceals or reduces the appearance of fine lines and/or wrinkles, or improves skin texture or smoothness.

Antibiotic: A chemical substance capable of treating bacterial infections by inhibiting the growth of, or by destroying existing colonies of bacteria and other microorganisms.

Anti-Fungal Agent: An active agent capable of inhibiting the growth of or destroying fungi.

Anti-Histamine: A drug that inhibits the action of histamine in the body by blocking the receptors of histamine. Exemplary anti-histamines include, but are not limited to, Diphenhydramine, Desloratidine and Loratidine, which are tricyclic H1 antihistamines used to treat allergies effective in doses from about 2 mg to about 10 mg, and Cetirizine, which is a second generation antihistamine used for the treatment of hay fever, allergies, angioedema and hives, effective in doses from about 2 mg to about 10 mg.

Anti-inflammatory agent: An active agent that reduces inflammation and swelling.

Anti-Oxidant: An active agent that inhibits oxidation or reactions promoted by oxygen or peroxides.

Anti-Protozoal Agent: An active agent capable of inhibiting the growth of or destroying protozoa microorganisms.

Antipruritic Agent: An active agent that reduces, eliminates or prevents itching.

Anti-Viral Agent: An active agent that inhibits the replication of or destroys viruses.

Bioadhesive: A polymer that exhibits a pressure-sensitive character of adhesion toward highly hydrated biological surfaces such as the hydrated skin. Exemplary bioadhesive polymers include chitosan, polycarbophil (polycyclic acid cross-linked with divinyl glycol, carbopol/carbomer (carboxy polymethylene), hydroxypropylmethyl cellulose HPMC (cellulose 2-hydroxypropylmethyl ether); hydroxyethyl cellulose; xanthan gum; guar gum; hydroxypropyl guar; chitosan; sodium alginate; carrageenan; poly (hydroxyl butyrate), poly (e-caprolactone) and copolymers; and poly (ortho esters).

Chemotherapeutic agent or Chemotherapy: A chemical agent with therapeutic usefulness in the treatment of diseases characterized by abnormal cell growth. Such diseases include tumors, neoplasms, and cancer. In one example, a chemotherapeutic agent is a radioactive compound. In one example, a chemotherapeutic agent is a biologic, such as a monoclonal antibody. In some examples, a subject treated with an active agent using the disclosed methods, is, will be, or was previously treated with chemotherapy. Exemplary chemotherapeutic agents are provided in Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993).

Contacting: Placement in direct physical association; includes both in solid and liquid form. Contacting can occur in vitro with isolated cells (for example in a tissue culture dish or other vessel) or in vivo by administering an active agent to a subject.

Control: A reference standard. In some examples, a control is a known value or range of values, such as one indicative of a non-anemic or an anemic subject. In some examples, a control is a value or range of values, indicating a response in the absence of a therapeutic agent.

Crosslinked: A composition containing intramolecular and/or intermolecular crosslinks, whether arising through covalent or non-covalent bonding. "Non-covalent" bonding includes both hydrogen bonding and electrostatic (ionic) bonding.

Drug or Active Agent: A chemical substance or compound that induces a desired pharmacological or physiological effect, and includes agents that are therapeutically effective, prophylactically effective, or cosmeceutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs, and the like. Suitable active agents that may be incorporated into the transdermal drug delivery systems provided herein and delivered transdermally include, but are not limited to, adrenergic agents; adrenocortical steroids; adrenocortical suppressants; alcohol deterrents; aldosterone antagonists; amino acids; ammonia detoxicants; anabolic agents; analeptic agents; analgesic agents; androgenic agents; anesthetic agents; anorectic compounds; anorexic agents; antagonists; anterior pituitary activators and anterior pituitary suppressants; anti-acne agents; anti-adrenergic agents; anti-allergic agents; anti-amebic agents; anti-androgen agents; anti-anemic agents; anti-anginal agents; anti-anxiety agents; anti-arthritic agents; antiasthmatic agents and other respiratory drugs; anti-atherosclerotic agents; anti-bacterial agents; anti-cancer agents, including antineoplastic drugs, and anti-cancer supplementary potentiating agents; anticholinergics; anticholelithogenic agents; anti-coagulants; anti-coccidal agents; anticonvulsants; anti-depressants; anti-diabetic agents; antidiarrheals; anti-diuretics; antidotes; anti-dyskinetics agents; anti-emetic agents; anti-epileptic agents; anti-estrogen agents; anti-fibrinolytic agents; anti-fungal agents; antiglaucoma agents; antihelminthics; anti-hemophilic agents; anti-hemophilic Factor; anti-hemorrhagic agents; antihistamines; anti-hyperlipidemic agents; anti-hyperlipoproteinemic agents; antihypertensive agents; anti-hypotensives; anti-infective agents such as antibiotics and antiviral agents; anti-inflammatory agents, both steroidal and non-steroidal; anti-keratinizing agents; anti-malarial agents; antimicrobial agents; anti-migraine agents; anti-mitotic agents; anti-mycotic agents; antinauseants; antineoplastic agents; anti-neutropenic agents; anti-obsessional agents; anti-parasitic agents; antiparkinsonism drugs; anti-pneumocystic agents; anti-proliferative agents; anti-prostatic hypertrophy drugs; anti-protozoal agents; antipruritics; anti-psoriatic agents; antipsychotics; antipyretics; antispasmodics; anti-rheumatic agents; anti-schistosomal agents; anti-seborrheic agents; anti-spasmodic agents; anti-tartar and anti-calculus agents; anti-thrombotic agents; anti-tubercular agents; antitussive agents; anti-ulcerative agents; anti-urolithic agents; antiviral agents; GERD medications, anxiolytics; appetite suppressants; attention deficit disorder (ADD) and attention deficit hyperactivity disorder (ADHD) drugs; bacteriostatic and bactericidal agents; benign prostatic hyperplasia therapy agents; blood glucose regulators; bone resorption inhibitors; bronchodilators; carbonic anhydrase inhibitors; cardiovascular preparations including anti-anginal agents, anti-arrhythmic agents, beta-blockers, calcium channel blockers, cardiac depressants, cardiovascular agents, cardioprotectants, and cardiotonic agents; central nervous system (CNS) agents; central nervous system stimulants; choleretic agents; cholinergic agents; cholinergic agonists; cholinesterase deactivators; coccidiostat agents; cognition adjuvants and cognition enhancers; cough and cold preparations, including decongestants; depressants; diagnostic aids; diuretics; dopaminergic agents; ectoparasiticides; emetic agents; enzymes which inhibit the formation of plaque, calculus or dental caries; enzyme inhibitors; estrogens; fibrinolytic agents; fluoride anticavity/antidecay agents; free oxygen radical scavengers; gastrointestinal motility agents; genetic materials; glucocorticoids; gonad-stimulating principles; hair growth stimulants; hemostatic agents; herbal remedies; histamine H2 receptor antagonists; hormones; hormonolytics; hypnotics; hypocholesterolemic agents; hypoglycemic agents; hypolipidemic agents; hypotensive agents; HMGCoA reductase inhibitors; immunizing agents; immunomodulators; immunoregulators; immunostimulants; immunosuppressants; impotence therapy adjuncts; inhibitors; keratolytic agents; leukotriene inhibitors; LHRH agonists; liver disorder treatments; luteolysin agents; memory adjuvants; mental performance enhancers; metal chelators such as ethylenediaminetetraacetic acid, tetrasodium salt; mitotic inhibitors; mood regulators; mucolytics; mucosal protective agents; muscle relaxants; mydriatic agents; narcotic antagonists; nasal decongestants; neuroleptic agents; neuromuscular blocking agents; neuroprotective agents; nicotine; NMDA antagonists; non-hormonal sterol derivatives; nutritional agents, such as vitamins, essential amino acids and fatty acids;

ophthalmic drugs such as antiglaucoma agents; oxytocic agents; pain relieving agents; parasympatholytics; peptide drugs; plasminogen activators; platelet activating factor antagonists; platelet aggregation inhibitors; post-stroke and post-head trauma treatments; potentiators; progestins; prostaglandins; prostate growth inhibitors; proteolytic enzymes as wound cleansing agents; prothyrotropin agents; psychostimulants; psychotropic agents; radioactive agents; regulators; relaxants; repartitioning agents; scabicides; sclerosing agents; sedatives; sedative-hypnotic agents; selective adenosine A1 antagonists; serotonin antagonists; serotonin inhibitors; serotonin receptor antagonists; steroids, including progestogens, estrogens, corticosteroids, androgens and anabolic agents; smoking cessation agents; stimulants; suppressants; sympathomimetics; synergists; thyroid hormones; thyroid inhibitors; thyromimetic agents; tranquilizers; tooth desensitizing agents; tooth whitening agents such as peroxides, metal chlorites, perborates, percarbonates, peroxyacids, and combinations thereof; unstable angina agents; uricosuric agents; vasoconstrictors; vasodilators including general coronary, peripheral and cerebral; vulnerary agents; wound healing agents; xanthine oxidase inhibitors; and the like.

Effective amount or Therapeutically effective amount: The amount of a therapeutic agent (alone or with one or more other therapeutic agents) sufficient to induce a desired response, such as to prevent, treat, reduce and/or ameliorate the symptoms and/or underlying causes of any of a disorder or disease, or to increase the number of cells, such as to increase the proliferation of cells, including stem cells. In one example, an "effective amount" is sufficient to reduce or eliminate a symptom of a disease, such as a sign or symptom of allergic rhinitis. In another example, an effective amount is an amount sufficient to overcome the disease itself. In a further example, an effective amount of a therapeutic agent, such as an antihistamine, is an amount that produces a statistically significant decrease in the symptoms of a disease, such as allergic rhinitis, as compared to a control, such as a culture or subject not treated with an antihistamine or treated with vehicle alone.

The condition or disease, such as allergic rhinitis or urticaria, does not need to be completely inhibited for the pharmaceutical preparation to be effective. Treatment can include slowing the progression of the disease temporarily, but can also include halting or reversing the progression of the disease permanently. For example, a pharmaceutical preparation can alleviate one or more signs or symptoms associated with allergic rhinitis or urticaria by decreasing the symptoms by at least 20%, at least 50%, at least 60%, at least 70%, at least 80%, at least 90%, at least 95%, at least 98%, even at least 100%, as compared to the symptoms in the absence of the pharmaceutical preparation.

Effective amounts of a therapeutic agent, alone or with one or more other therapeutic agents, can be determined in many different ways, such as assaying for a reduction in of one or more signs or symptoms associated with the condition, such as allergic rhinitis or urticaria, in the subject or measuring the level of one or more molecules associated with the condition to be treated. Effective amounts also can be determined through various in vitro, in vivo or in situ assays, including the assays described herein.

Emulsifying Agents: Surfactants that reduce the interfacial tension between oil and water, minimizing the surface energy through formation of globules. Examples include, but are not limited to, glyceryl monostearate, methylcellulose, sodium lauryl sulfate, sodium oleate, sorbitan monopalmitate, sorbitan monostearate, sorbitan tristrearate, tragacanth, triethanolamine oleate, polyethylene sorbitan monolaurate, poloxamer, and any combination thereof.

Hydrogel: A water-swellable polymeric matrix that can absorb a substantial amount of water to form elastic gels. The matrix is a three-dimensional network of macromolecules held together by covalent or non-covalent crosslinks. Upon placement in an aqueous environment, dry hydrogels swell to the extent allowed by the degree of cross-linking.

Hydrogel Composition: A composition that either contains a hydrogel or is entirely composed of a hydrogel. Thus, "hydrogel compositions" encompass not only hydrogels per se but also compositions that comprise a hydrogel and one or more non-hydrogel components or compositions, e.g., hydrocolloids, which contain a hydrophilic component (which may contain or be a hydrogel) distributed in a hydrophobic phase.

Hydrophilic: A polymer, substance or compound capable of absorbing more than 10%/w of water at 100% relative humidity (rh).

Hydrophobic: A polymer, substance or compound capable of absorbing no more than 1%/w of water at 100% relative humidity (rh).

Hygroscopic: A polymer, substance or compound capable of absorbing more than 20 wt % of water at 100% relative humidity (rh).

Immune Response: The reaction to and interaction with substances interpreted by the body as not-self. The immune response depends on a functioning thymus and the conversion of stem cells to B and T lymphocytes. These lymphocytes contribute to antibody production, cellular immunity, and immunologic memory. Pathologic conditions associated with an abnormal immune response (immunopathy) may result from immuno-depression, excessive production of gamma globulins, overreaction to antigens of extrinsic origin, or abnormal response of the body to its own cells and tissues. Factors that may cause or contribute to suppression of the immune response include (1) congenital absence of the thymus or of the stem cells that are precursors of B and T lymphocytes; (2) malnutrition, in which there is a deficiency of the specific nutrients essential to the life of antibody-synthesizing cells; (3) cancer, viral infections, and extensive burns, all of which overburden the immune response mechanisms and rapidly deplete the supply of antigen-specific antibody; (4) certain drugs, including alcohol and heroin, some antibiotics, antipsychotics, and the antineoplastics used in the treatment of cancer. Overproduction of gamma globulins is manifested by an excessive proliferation of plasma cells (multiple myeloma). Hypersensitivity is the result of an overreaction to substances entering the body.

Inhibiting a disease or condition: Reducing, slowing, or even stopping the development of a disease or condition, for example, in a subject who is at risk for a disease or who has a particular disease, such as allergic rhinitis or urticaria.

Keratolytic Agent: An agent that that thins or softens the skin. Exemplary keratolytic agents include urea, lactic acid, allantoin, benzoyl peroxide, salicyclic acid, sulfur, tretinoin, fluorouracil, trichloroacetic acid, and glycolic acid.

Lipophilic: A substance or compound that has an affinity for a non-polar environment compared to a polar or aqueous environment.

Localized administration: The administration of a therapeutic agent in a particular location in the body.

Matrix: A three dimensional network of polymeric fibers that contains pores. The structural parameters of the pores, including the pore size, porosity, pore interconnectivity/tortuosity and surface area, affect how active agents dispersed in the matrix move in and out of the matrix.

Patch: A topical patch may be in multiple forms, including single and multi-layer drug-in-adhesive forms, matrix forms, and reservoir forms, and has a finite size and shape. Thus, the application area on the skin is determined by the dimensions of the patch, rather than by the dimensions of the affected site.

Permeation Enhancer: A natural or synthetic molecule that facilitates the transport of co-administered active agents across biological membranes.

pH Modifier: A molecule or buffer used to achieve desired pH control in a formulation. Exemplary pH modifiers include acids (e.g., acetic acid, adipic acid, carbonic acid, citric acid, fumaric acid, phosphoric acid, sorbic acid, succinic acid, tartaric acid, basic pH modifiers (e.g., magnesium oxide, tribasic potassium phosphate), and pharmaceutically acceptable salts thereof.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of the compositions herein disclosed (such as antihistamines). For example therapeutic agents can be administered in the presence of one or more pharmaceutically acceptable carriers, including a non-natural or natural pharmaceutically acceptable carrier molecule.

The nature of the carrier can depend on the particular mode of administration being employed. For instance, transdermal formulations usually include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Embodiments of other pharmaceutical compositions can be prepared with conventional pharmaceutically acceptable carriers, adjuvants, and counter-ions, as would be known to those of skill in the art.

Plasticizer: A material that, when added to a polymer, imparts an increase in flexibility, workability, and other properties to the finished product. Exemplary plasticizers include, but are not limited to, glycerol, sorbitol, polyethylene glycol, polypropylene glycol, polyethylene-propylene glycol, and any combination thereof.

Polymer: Includes homopolymers, linear and branched polymer structures, crosslinked polymers, copolymers (which may or may not be crosslinked), block copolymers, alternating copolymers, random copolymers, and the like. Oligomers are polymers having a molecular weight below about 1000 Da.

Polyvinylpyrrolidone or PVP: A synthetic polymer consisting of linear 1-vinyl-2-pyrrolidinone groups; it is produced commercially as a series of products having mean molecular weights ranging from about 10,000 to about 700,000. The viscosity of solutions containing 10% or less PVP is essentially the same as that of water; solutions more concentrated than 10% become more viscous, depending on the concentration and molecular weight of the polymer used.

Pressure sensitive adhesive (PSA): A polymer material, which forms a strong adhesive bond to any surface with application of very slight external pressure over a short period of time (e.g., 1-5 seconds).

Scanning Electron Microscope (SEM): a technique that scans a focused electron beam over a surface to create an image. The electrons in the beam interact with the sample, producing various signals that can be used to obtain information about the surface topography and composition. The electron beam is scanned in a raster scan pattern, and the beam's position is combined with the detected signal to produce an image. SEM can achieve resolution better than 1 nanometer. Specimens can be observed in high vacuum in conventional SEM, or in low vacuum or wet conditions in variable pressure or environmental SEM, and at a wide range of cryogenic or elevated temperatures with specialized instruments.

Skin: The largest organ in the body consisting of several layers. The skin plays an important role in biologic homeostasis, and is comprised of the epidermis and the dermis. The epidermis, which is composed of several layers beginning with the stratum corneum, is the outermost layer of the skin, and the deep dermis is the innermost skin layer. The skin has multiple functions, including thermal regulation, metabolic function (vitamin D metabolism), and immune functions. In humans, the usual thickness of the skin is 1-2 mm, although in some areas the skin may be more than 5 mm thick.

The epidermis provides the body's buffer zone against the environment and protection from trauma, excludes toxins and microbial organisms, and constitutes a semi-permeable membrane. The stratum corneum is an avascular, multilayer structure that functions as a barrier to the environment and prevents trans-epidermal water loss. Below the stratum corneum are the stratum lucidum, stratum granulosum, stratum germinativum, and stratum basale, each containing living cells with specialized functions. Dermal appendages, which include hair follicles, sebaceous and sweat glands, fingernails, and toenails, originate in the epidermis and protrude into the dermis hair follicles. The sebaceous glands are responsible for secretions that lubricate the skin, and sweat gland secretions control skin pH to prevent dermal infections. The sweat glands, dermal blood vessels, and small muscles control temperature on the surface of the body. Nerve endings in the skin include receptors for pain, touch, heat, and cold. The basement membrane separates and connects the epidermis and dermis. The dermis is a vascular structure that supports and nourishes the epidermis. In addition, there are sensory nerve endings in the dermis that transmit signals regarding pain, pressure, heat, and cold. The superficial dermis consists of extracellular matrix (collagen, elastin, and ground substances) and contains blood vessels, lymphatics, epithelial cells, connective tissue, muscle, fat, and nerve tissue. The vascular supply of the dermis is responsible for nourishing the epidermis and regulating body temperature. Fibroblasts are responsible for producing the collagen and elastin components of the skin, which give the skin its turgor. Fibronectin and hyaluronic acid are secreted by the fibroblasts. The deep dermis is located over the subcutaneous fat; it contains larger networks of blood vessels and collagen fibers to provide tensile strength. It also consists of fibroelastic connective tissue, which is composed mainly of collagen.

Skin Simulating Membrane: A semi-permeable membrane used to replicate the skin in diffusion testing.

Subject: A living multi-cellular vertebrate organism, a category that includes human and non-human mammals, as well as birds (such as chickens and turkeys), fish, and reptiles. Exemplary subjects include mammals, such as human and non-human primates, rats, mice, dogs, cats, rabbits, cows, pigs, goats, horses, and the like.

Surface or Body Surface: A surface located on the human body or within a body orifice. Thus, a "body surface" includes, by way of example, skin, teeth, skin or mucosal tissue, including the interior surface of body cavities that have a mucosal lining.

Tacky: May be quantified using the values obtained in a PKI tack determination, a TRBT tack determination, or a PSA tack determination/Polyken Probe (Solutia, Inc.). The term "substantially nontacky" means a hydrogel composition that has a tack value that is less than about 25 g/cm/sec; "slightly tacky" means a hydrogel composition that has a tack value in the range of about 25 g/cm/sec to about 100 g/cm/sec; and "tack" means a hydrogel composition that has a tack value of at least 100 g/cm/sec.

Transdermal Drug Delivery System: A system that administer an active agent to the skin or mucosa of an individual so that the drug passes through the skin tissue and into the individual's blood stream. The term "transdermal" may also include "transmucosal" drug administration, i.e., administration of a drug to the mucosal (e.g., sublingual, buccal, vaginal, rectal, urethral) surface of an individual so that the drug passes through the mucosal tissue and into the individual's blood stream. For example, a transdermal drug delivery device may contain a matrix, in which one or more drugs or active agents are dispersed, a backing layer, a rate-controlling membrane, and an adhesive means for affixing the system to a body surface.

Topical administration: Delivery of an active agent to a body surface, such as, the skin or mucosa, as in, for example, topical drug administration in the prevention or treatment of various skin disorders, the application of cosmetics (including moisturizers, masks, sunscreens, etc.), and the like. Topical administration, in contrast to transdermal administration, provides a local rather than a systemic effect.

Under conditions sufficient to: A phrase that is used to describe any environment that permits the desired activity.

Water-Insoluble: A polymer, compound or composition whose solubility in water is less than 5%/w, less than 3%/w, or less than 1%/w, measured in water at 20° C.

Water-Swellable: A polymer, substance or compound capable of absorbing an amount of water greater than at least 25%/w of its own weight, or greater than at least 50%/w, upon immersion in an aqueous medium.

Transdermal Drug Delivery System

A transdermal drug delivery system is disclosed. The disclosed transdermal drug delivery system comprises a patch having a diameter between 1 and 8 cm in length and a surface area between 4 and 7.5 cm$^2$. The small size of the patch enables the water- and sweat-resistant transdermal drug delivery system to provide a large surface-to-volume ratio, such that large amounts of drugs may be delivered through the skin into the blood stream, and the surface area of the skin required for administration is minimized. The transdermal delivery system has an onset of action within 5 to 15 minutes, and allows about 65% to about 100% of one or more drugs to diffuse into the skin of a mammal within 8 to 24 hours.

The transdermal drug delivery system provided herein is water-and sweat-resistant. The patch does not come off upon contact with water (e.g. sweating, showering). Rather, the hydrophilicity of the patch leads to higher adhesion onto the skin when wet. Additionally, water may decrease the viscosity of the patch, allowing it to better flow into pockets in the skin and to increase the surface area of adhesion.

The transdermal drug delivery system disclosed herein is also particularly suitable for use on sensitive skin. The patch comprises a monolithic layer of about 1 to 5 mm in width, wherein the monolithic layer comprises 10-30% (w/w) of a bioadhesive polymer; 10-40% (w/w) of a film-forming agent; 10-60% (w/w) of a plasticizer; 1-20% (w/w) of a naturally occurring polysaccharide; 10-50% (w/w) of a keratolytic agent; and 1-60% (w/w) of one or more active agents. The particular choice of the patch components and their ratio ensures that the patch causes no irritation to the skin, and no redness or swelling even after prolonged periods of use. Therefore, the disclosed transdermal drug delivery system is particular suitable for use in subjects with sensitive skin, such as elderly and pediatric populations.

In some examples, the bioadhesive polymer may include chitosan, hydroxypropylmethyl cellulose, hydroxyethyl cellulose, xanthan gum, guar gum, sodium alginate, or a combination thereof. In some examples, the film-forming agent may include polyvinyl alcohol, polyvinyl pyrrolidone, carrageenan, gelatin, dextrin, polyethylene oxide, guar gum, xanthan gum, or a combination thereof. In some additional examples, the plasticizer may include glycerol, sorbitol, polyethylene glycol, polypropylene glycol, polyethylene-propylene glycol, or a combination thereof. In some other examples, the naturally occurring polysaccharide may include agar, alginate, chitin, glucomannan, gellan gum, gelatin, gum guar, gum Arabic, locust bean gum, pectin, xanthan, or a combination thereof. In some examples, the keratolytic agent may include urea, lactic acid, allantoin, benzoyl peroxide, salicyclic acid, or a combination thereof.

In some examples, the patch comprises chitosan (10-30% w/w), polyvinylpyrrolidone (PVP) (10-40% w/w), glycerol (10-60% w/w), gum Arabic (less than 20% w/w), and lactic acid (10-50% w/w). Without being bound to any theory, chitosan increases viscosity and decreases skin irritation; PVP increases cohesiveness and water resistance, and decreases adhesiveness; glycerol increases adhesiveness and reduces cohesion and rigidity; gum Arabic increases adhesion and reduces cohesion; and lactic acid increases homogeneity and decreases skin irritation and cohesion. Moreover, the patch possesses great adhesive strength, with a peel rate of approximately 320 mm/min.

The disclosed transdermal drug delivery system can deliver different small molecules with a wide variety of functional groups including, but not limited to, aliphatic chains, aromatic rings, pyridine rings, purine rings, imidazole rings, halogenated aromatic rings, alcohols, ethers, carboxylic acids, aldehydes, ketones, esters, primary amines, secondary amines, and tertiary amines, primary amides, secondary amides and tertiary amides, thiols, sulfines, sulfones, sulfonamides, thioamides, sulfonoesters and thioesters among others.

The patch is capable of holding and delivering a number of drugs including, but not limited to, diphenhydramine, desloratadine, cetirizine, dalfampridine, amitriptyline, etoricoxib, glicazide, lisinopril, tramadol, propranolol, ondansetron, diphenhydramine, fluoxetine, duloxetine, levodopa, loratadine, orlistat, venlaflaxine, pioglitzazone, fingolimod, escitalopram, carbidopa, alprazolam, clonazepam, modafinil, armodafinil, dextroamphetamine, fluorenol, aniracetam, coluracetam, fasoracetam, nefiracetam, oxiracetam, phenylpiracetam, piracetam, pramiracetam, adrafinil, alpha-GPC, choline bitartrate, citicoline, creatine, tyrosine, bromantane, cotinine, L-theanine, N-acetylcysteine, noopept, prolintane, tianeptine, buproprion, citalopram, sertraline, trazodone, mirtazapine, paroxetine, amitryptyline, lamotrigine, nortriptyline, quetiapine, tramadol, doxepin, olanzapine, risperidone, imipramine, lithium, simvastatin, pravastatin, lovastatin, rosuvastatin, prednisone, dimethylx fumarate, mitoxantrone, natalizumab, teriflunomide, dexamethasone, prednisolone, valacyclovir, azathioprine, cyclophosphamide, mycophenolate, haloperidole, esomeprazole, rivarocaban, oxycodone, valsartan, memantine, quetiapine, sevelamer, budenoside, hydrocodone, doxycycline, eszopiclone, fenofibrate, metoprolol, valproate, omeprazole, metformin, amlodipine, losartan, zolpidem, hydrochlorothiazide, pantoprazole, amoxicillin, tamsulosin, fluticasone, carvedilol, warfarin, meloxicam, clopidogrel, atenolol, tadalafill, salbutamol, albuterol, cyclobenzaprine, capsaicin, celecoxib, baclofen, acrivastine, pseudoephedrine, loxapine, riociguat, lubiprostone, prostacyclin, benzphetamine, bortezomib, busulfan, cinacalet, nadolol, fenoldopam, cyproheptadine, cysteamine, decitabine, darifenacin, dacogen, desvenlaxafine, amfepramone, quazepam, famotidine, prasugrel, eletriptan, eplernone, perphenazine, melphalan, exemestane, ezetimibe, penciclovir, fenolodpam, fesoterodine, fluoricortisone, hydrocodone, frovatriptan, tigecycline, ziprasidone, glipizide, miglitol, guanethidine, guanfacine, camptothecin, hyoscyamine, ibrutinib, ibutilide and iloprost.

In some examples, the active agent or drug is one or more of Diphenhydramine, Desloratadine, Cetirizine, Loratadine, Trihexyphenidyl, Asenapine, Prostacyclin, Buspirone, Butorphanol, Captopril, Carbidopa, Albuterol, Naltrexonelvabradine, Dexamethasone, Phenylephrine, Fluocinolone acetonide, Dexlansoprazole, Furosemide, Isradipine, Venlafaxine, and Enalapril. Table 1 below shows the structure of some of the drugs that may be transdermally delivered by the transdermal drug delivery system provided herein.

TABLE 1

| Drug Name | Molecular Structure | Molecular Weight (Da) | Trade Name | Medical Purpose |
|---|---|---|---|---|
| Cetirizine dihydrochloride | 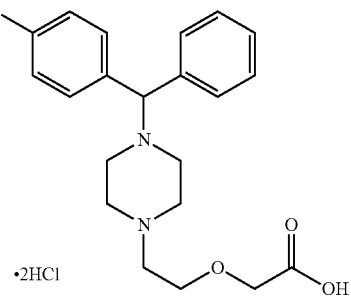 | 461.81 | Zyrtec ®, others | Allergies |

TABLE 1-continued

| Drug Name | Molecular Structure | Molecular Weight (Da) | Trade Name | Medical Purpose |
|---|---|---|---|---|
| Desloratadine | 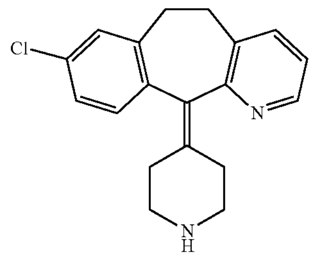 [SMILES: Clc1ccc2c(c1)CCc1cccnc1C2=C1CCNCC1] | 310.82 | Clarinex ®, Aerius ®, others | Allergies |
| 4-Aminopyridine | 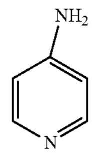 | 94.11 | Ampyra ®, Fampyra ®, others | Multiple sclerosis |
| Aripiprazole | 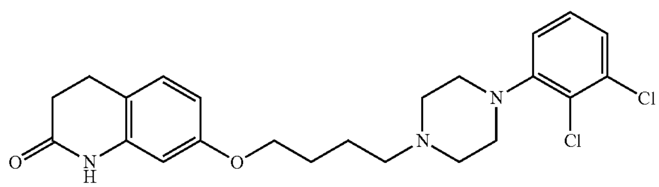 [SMILES: O=C1CCc2ccc(OCCCCN3CCN(c4cccc(Cl)c4Cl)CC3)cc2N1] | 448.39 | Abilify ®, others | Schizophrenia, bipolar disorder |
| Escitalopram Oxalate | 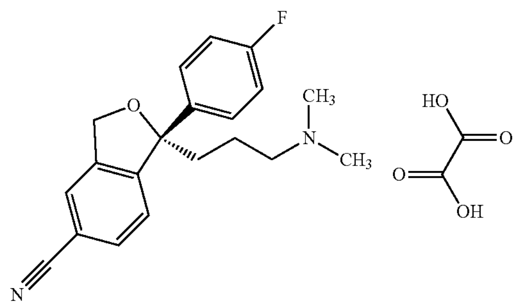 | 414.43 | Lexapro ®, others | Depression, anxiety |

The active agents or drugs may be released from the polymeric matrix in the patch by diffusion. The release may be a controlled release, a delayed release, or a sustained release. The concentration of the one or more active agents or drugs in the patch is at least 1% w/w of the composition, at least 2% w/w of the composition, at least 3% w/w of the composition, at least 4% w/w of the composition, at least 5% w/w of the composition, at least 6% w/w of the composition, at least 7% w/w of the composition, at least 8% w/w of the composition, at least 9% w/w of the composition, at least 10% w/w of the composition; at least 11% w/w of the composition; at least 12% w/w of the composition; at least 13% w/w of the composition; at least 14% w/w of the composition; at least 15% w/w of the composition; at least 16% w/w of the composition; at least 17% w/w of the composition; at least 18% w/w of the composition; at least 19% w/w of the composition; at least 20% w/w of the composition, at least 30% w/w of the composition, at least 40% w/w of the composition, at least 50% w/w of the composition, or at least 60% w/w of the composition.

The content of the one or more active agents or drugs transdermally delivered to the skin and their permeation/flux into the skin may be measured as a function of time. In some examples, the flux is determined using an artificial skin simulating membrane or human cadaver skin attached to a Franz diffusion cell, as described in the examples.

Optionally, the disclosed transdermal drug delivery system may comprise a backing layer and trimmed to a desired size. Suitable materials for the backing layer include, but are not limited to, Teflon, metal foils, metalized polyfoils, composite foils or films containing polyester, such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. Additionally, the backing layer may include various foams, such as, but not limited to, polyolefin foams, polyvinyl chloride foams, polyurethane foams, and polyethylene foams.

The backing layer may contain occlusive agents or be substantially impermeable to the components of the patch. In some examples, the transdermal drug delivery system is occlusive to one or more molecules, including, but not limited to, caffeine, aripiprazole, theophylline, dyphilline, pentoxifyline, enprofylline, aminophylline, oxtriphylline, theobromine, propentofylline, xanthinol, doxofylline, pamabrom, lisofylline, ganciclovir, fenethylline, xanthine, uric acid, rolofylline, reproterol, cafedrine and theodrenaline, and any combination thereof.

The transdermal drug delivery system provided herein may be applied to the skin, deliver one or more drugs, and be left on the skin for at least 1 hour, at least 2 hours, at least 3 hours, at least 4 hours, at least 5 hours, at least 6 hours, at least 7 hours, at least 8, at least 9, at least 10, at least 11, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, at least 49 hours, at least 50 hours, at least 51 hours, at least 52 hours, at least 53 hours, at least 54 hours, at least 55 hours, at least 56 hours, at least 57 hours, at least 58 hours, at least 59 hours, at least 60 hours, at least 61 hours, at least 62 hours, at least 63 hours, at least 64 hours, at least 65 hours, at least 66 hours, at least 67 hours, at least 68 hours, at least 69 hours, at least 70 hours, at least 71 hours, at least 72 hours, at least 73 hours, at least 74 hours, at least 75 hours, at least 76 hours, at least 77 hours, at least 78 hours, at least 79 hours, at least 80 hours, at least 81 hours, at least 82 hours, at least 83 hours, at least 84 hours, at least 85 hours, at least 86 hours, at least 87 hours, at least 88 hours, at least 89 hours, at least 90 hours, at least 91 hours, at least 92 hours, at least 93 hours, at least 94 hours, at least 95 hours, at least 96 hours, at least 97 hours, at least 98 hours, at least 99 hours, at least 100 hours, at least 110 hours, or at least 120 hours before it is removed.

The disclosed transdermal drug delivery system may further comprise a penetration enhancer. Non-limiting examples of penetration enhancers include glycerol monolaurate (GML), lecithin, or a vegetable oil, for example, safflower oil, cottonseed oil and corn oil.

The disclosed transdermal drug delivery system may further comprise an anti-oxidant. Exemplary anti-oxidants include, but are not limited to, ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, bioflavonoids, curcumin, lysine, methionine, proline, superoxide dismutase, silymarin, tea extracts, grape extracts, melanin, and rosemary extracts. The antioxidant may be present at a concentration from 0.1% to 10% w/w of the patch.

The patch may further comprise auxiliary agents, e.g., lubricants, preservatives, stabilizers, wetting agents, emulsifiers, salts for influencing osmotic pressure, buffers, colorants, flavorants and/or fragrances and the like which do not deleteriously react with the active compounds.

Thus, the water- and sweat-resistant transdermal drug delivery system provided herein provides a dosage form that achieves quick delivery through the skin into the blood stream, reduces common side effects and improves patient compliance.

Method of Making the Disclosed Transdermal Drug Delivery System

Also provided herein is a method of making a water- and sweat-resistant transdermal drug delivery system. The method comprises first adding a film-forming agent and a plasticizer to water and stirring the mixture at room temperature (25° C.); gradually adding a bioadhesive polymer and a naturally occurring polysaccharide and stir the mixture until the bioadhesive polymer is dissolved and viscosity is reduced; then adding a film-forming agent and a keratolytic agent and stirring for 2-5 hours until an even mixture is obtained; adding one or more active agents and stirring the mixture for 1-4 hours to obtain a formulation; and optionally casting the formulation onto an array of backing layers and baking the backing layers at 80° C. for 4-8 hours to obtain a patch with a backing layer.

The bioadhesive polymer may include chitosan, hydroxypropylmethyl cellulose, hydroxyethyl cellulose, xanthan gum, guar gum, sodium alginate, or a combination thereof. The film-forming agent may include polyvinyl alcohol, polyvinyl pyrrolidone, carrageenan, gelatin, dextrin, polyethylene oxide, guar gum, xanthan gum, or a combination thereof. In some additional examples, the plasticizer may include glycerol, sorbitol, polyethylene glycol, polypropylene glycol, polyethylene-propylene glycol, or a combination thereof. The naturally occurring polysaccharide may include agar, alginate, chitin, glucomannan, gellan gum, gelatin, gum guar, gum Arabic, locust bean gum, pectin, xanthan, or a combination thereof. The keratolytic agent may include urea, lactic acid, allantoin, benzoyl peroxide, salicyclic acid, or a combination thereof. In some examples, the patch comprises 10-30% (w/w) chitosan; 10-40% (w/w) polyvinylpyrrolidone; 10-60% glycerol; 1-20% (w/w) gum Arabic; and 10-50% (w/w) lactic acid.

In some examples, the disclosed transdermal drug delivery system may comprise a backing layer. Suitable materials for the backing layer include, but are not limited to, Teflon, metal foils, metalized polyfoils, composite foils or films containing polyester, such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. Additionally, the backing layer may include various foams, such as, but not limited to, polyolefin foams, polyvinyl chloride foams, polyurethane foams, and polyethylene foams.

In some examples, the provided method may further comprise adding 2-15% (w/w) of one or more fatty acids. The fatty acids include, but are not limited to, tartaric acid, oleic acid, lauric acid, maleic acid, and any combination thereof. In some examples, the provided method may further comprise adding 2-15% (w/w) of one or more essential oils. Essential oils include, but are not limited to, L-menthol, chuanxiong oil, clove oil, cinnamon oil, turpentine oil, eucalyptus oil, and any combination thereof.

The provided method produces a water- and sweat-resistant transdermal drug delivery system that may deliver a great variety of active agents into the skin. In some example, only one active agent at the time is delivered into the skin. In other examples, a combination of active agents is delivered into the skin, either sequentially or contemporaneously. Examples of active agents include, but are not limited to, one or more antihistamines, potassium channel blockers, analgesic agents, antidiabetic agents, pain-relief agents, antidepressant agents, antipsychotic agents, anti-Parkinsonian agents, vasodilators, diuretics, calcium channel blockers, anti-acne agents, anti-aging agents, antibiotic agents, antifungal agents, ACE inhibitors, GERD medications, anti-inflammatory agents, opioids, anti-asthma agents, corticosteroids, nicotinic cholinergic receptor agonists, anti-oxidant agents, antiprotozoal agents, antipruritic agents, antiviral agents, chemotherapeutic agents, immunomodulatory agents, keratolytic agents, retinoids, and central nervous system stimulants. Thus, in some examples, the active agent is on or more of Diphenhydramine, Desloratadine, Cetirizine, Loratadine, Trihexyphenidyl, Asenapine, Prostacyclin, Buspirone, Butorphanol, Captopril, Carbidopa, Albuterol, Naltrexone, Ivabradine, Dexamethasone, Phenylephrine, Fluocinolone acetonide, Dexlansoprazole, Furosemide, Isradipine, Venlafaxine, and Enalapril.

Exemplary antihistamines include, but are not limited to, Diphenhydramine, Loratadine, Desloratadine, and Cetirizine. Exemplary antidepressants and anti-anxiety agents include, but are not limited to, Sertraline, Fluoxetine, Paroxetine, Venlaxafine, Duloxetine, Escitalopram Oxalate, Alprazolam, and Lorazepam. Exemplary ADHD medications include, but are not limited to, amphetamine aspartate, dextroamphetamine, methylphenidate hydrochloride, dexmethylphenidate hydrochloride, and amitriptyline. Exemplary Anti-Parkinson's medications include, but are not limited to, Levodopa, Carbidopa, Ropinirole, Pramipexole, Rotigotine, Apomorphine, Selegine Hydrochloride, Rasagiline, and Benztropine. Exemplary Multiple Sclerosis Medications include, but are not limited to, Teriflunomide, Dalfampridine, Dimethyl Fumarate, Natalizumab, Fingolimod, and Glatiramer Acetate. Exemplary Alzheimer's Medications include, but are not limited to, Donezepil, Rivastigmine, and Galantamine. Exemplary analgesics include, but are not limited to, Methadone, Hydromorphone, Oxymorphone, Buprenorphine, Hydrocodone, Morphine, and Hydrocodone. Exemplary GERD medications include, but are not limited to, esomeprazole, omeprazole, and pantoprazole. Exemplary anti-cholesterol agents include, but are not limited to, ondansentron, pioglitazone, orlistat, lenalidomide, sofusbovir, rosuvastatin, amlodipine, simvastatin, and metformin.

The method provided herein may additionally produce a water- and sweat-resistant transdermal drug delivery system that comprises a patch that is occlusive to one or more molecules. These molecules include, but are not limited to, caffeine, aripiprazole, theophylline, dyphilline, pentoxifyline, enprofylline, aminophylline, oxtriphylline, theobromine, propentofylline, xanthinol, doxofylline, pamabrom, lisofylline, ganciclovir, fenethylline, xanthine, uric acid, rolofylline, reproterol, cafedrine and theodrenaline, and any combination thereof.

The method provided herein produces a water- and sweat-resistant transdermal drug delivery system that has a diameter between 1 and 8 cm in length, a surface area between 4 and 8 cm$^2$ and an onset of action within 15 minutes of application to the skin of a mammal, and it sustainably delivers on or more active agents for 8-24 hours. The patch within the transdermal delivery system produced by the provided method has excellent adhesive strength, as shown by a peel rate of about 320 mm/min, and allows diffusion of 65% to 100% of the active agent into the skin of a mammal within 8 to 24 hours. The mammal can be an animal or a human subject.

Methods of Treatment

Methods of treatment using the transdermal drug delivery system provided herein are also disclosed. Provided herein is a method of treating seasonal allergic rhinitis in a subject in need thereof, wherein the method comprises applying the water- and sweat-resistant transdermal drug delivery system comprising one or more antihistamines to the subject's skin, and maintaining the water- and sweat-resistant transdermal drug delivery system in contact with the skin of the subject for 8-24 hours, thereby treating seasonal allergic rhinitis in the subject. Exemplary antihistamines include, but are not limited to, diphenhydramine, desloratidine, cetirizine, loratadine, and any combinations thereof. In some examples, the release rate of the one or more antihistamines from the patch is 600 µg/cm$^2$/hour during the first hour of applying the patch. In some examples, the release rate of the one or more antihistamines from the patch is at least 100 µg/cm$^2$/hour during the entire time of applying the patch.

Also provided herein is a method of treating seasonal chronic idiopathic urticaria in a subject in need thereof, wherein the method comprises applying the water- and sweat-resistant transdermal drug delivery system comprising one or more antihistamines to the subject's skin, and maintaining the water- and sweat-resistant transdermal drug delivery system in contact with the skin of the subject for 8-24 hours, thereby treating seasonal chronic idiopathic urticaria in the subject. Exemplary antihistamines include, but are not limited to, diphenhydramine, desloratidine, cetirizine, loratadine, and any combinations thereof. In some examples, the release rate of the one or more antihistamines from the patch is 600 µg/cm$^2$/hour during the first hour of applying the patch. In some examples, the release rate of the one or more antihistamines from the patch is at least 100 µg/cm$^2$/hour during the entire time of applying the patch.

Transdermal Drug Delivery System Comprising One or More Antihistamines

Also provided herein is a water- and sweat-resistant transdermal drug delivery system, wherein the monolithic layer comprises 10-30% (w/w) chitosan; 10-40% (w/w) polyvinylpyrrolidone; 10-60% glycerol; 1-20% (w/w) gum Arabic; 10-50% (w/w) lactic acid, and a therapeutically effective amount of one or more antihistamines. Exemplary antihistamines include, but are not limited to, diphenhydramine, desloratidine, cetirizine, loratadine, and any combinations thereof. In some examples, the release rate of the one or more antihistamines from the patch is 600 µg/cm$^2$/hour during the first hour of applying the patch. In some examples, the release rate of the one or more antihistamines from the patch is at least 100 µg/cm$^2$/hour during the entire time of applying the patch. In some examples, the monolithic layer may further comprise 2-15% (w/w) of one or more fatty acids. The fatty acids include, but are not limited to, tartaric acid, oleic acid, lauric acid, maleic acid, and any combination thereof. In some examples, the monolithic layer may further comprise 2-15% (w/w) of one or more essential oils. Essential oils include, but are not limited to, L-menthol, chuanxiong oil, clove oil, cinnamon oil, turpentine oil, eucalyptus oil, and any combination thereof.

EXAMPLES

Example 1: Method of Making a Transdermal Drug Delivery System

A liquid matrix comprising a layer of chitosan dissolved in lactic acid, glycerol and polyvinyl pyrrolidone is poured into a Teflon backing layer and solidified by solvent evaporation. The patch thus formed is circular, and has a diameter of 4 cm. The backing layer and the matrix are equal in size.

Figure 2:
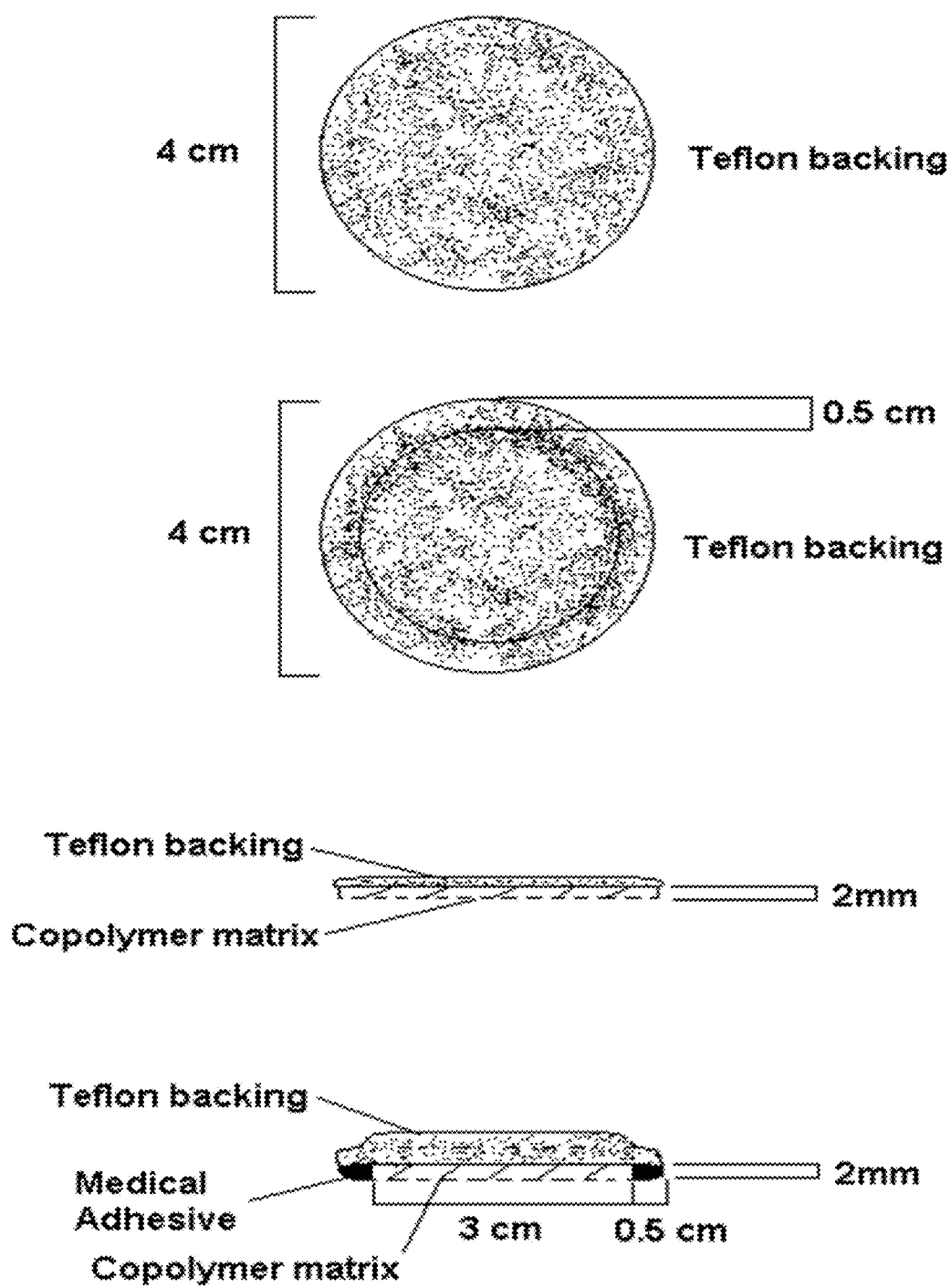
FIG. 2 provides top views and lateral views of transdermal drug delivery systems provided herein. First from the top of the figure: a top view of a transdermal drug delivery system provided herein. The transdermal drug delivery system comprises a drug dispersed in an adhesive polymer matrix, which comprises a layer of chitosan dissolved in lactic acid, glycerol and polyvinyl pyrrolidone (PVP). The liquid matrix is poured into the backing layer and solidified by solvent evaporation. The patch is circular, and has a diameter of 4 cm. The backing layer and the matrix are equal in size. The chitosan and polyvinyl pyrrolidone matrix has a final thickness of approximately 1 mm. Second from the top of the figure: a top view of a transdermal drug delivery system provided herein. The transdermal drug delivery system comprises a drug dispersed in an adhesive polymer matrix, which comprises a layer of chitosan dissolved in lactic acid, glycerol and polyvinyl pyrrolidone (PVP). The liquid matrix is poured into the backing layer and solidified by solvent evaporation. The matrix size is reduced to 3 cm, and then mounted on an additional backing layer, which has a diameter of 4 cm. The edges of the backing layer are casted with a medical adhesive to match the thickness of the matrix. Third from the top of the figure: a lateral view of a transdermal drug delivery system provided herein. The transdermal drug delivery system comprises a drug dispersed in an adhesive polymer matrix, which comprises a layer of chitosan dissolved in lactic acid, glycerol and polyvinyl pyrrolidone (PVP). The liquid matrix is poured into the backing layer and solidified by solvent evaporation. The patch is circular, and has a diameter of 4 cm. The backing layer flushes with the matrix. The chitosan and polyvinyl pyrrolidone matrix has a final thickness of approximately 1 mm. Fourth from the top of the figure: a lateral view of a transdermal drug delivery system provided herein. The transdermal drug delivery system comprises a drug dispersed in an adhesive polymer matrix, which comprises a layer of chitosan dissolved in lactic acid, glycerol and polyvinyl pyrrolidone (PVP). The liquid matrix is poured into the backing layer and solidified by solvent evaporation. The matrix size is reduced to 3 cm, and then mounted on an additional backing layer, which has a diameter of 4 cm. The edges of the backing layer are casted with a medical adhesive to match the thickness of the matrix.

The chitosan and polyvinyl pyrrolidone matrix has a final thickness of approximately 1 mm. See FIG. 2, first and third from top of figure.

In an alternative method, the transdermal drug delivery system comprises a drug dispersed in an adhesive polymer matrix, which comprises a layer of chitosan dissolved in lactic acid, glycerol and polyvinyl pyrrolidone. The liquid matrix is poured into a Teflon backing layer and solidified by solvent evaporation. The matrix size is reduced to 3 cm, and then mounted on an additional backing layer, which has a diameter of 4 cm. The edges of the Teflon backing layer are casted with a medical adhesive to match the thickness of the matrix. See FIG. 2, second and fourth from top of figure.

Example 2: In Vitro Drug Diffusion Through a Skin Simulating Membrane

Figure 3:
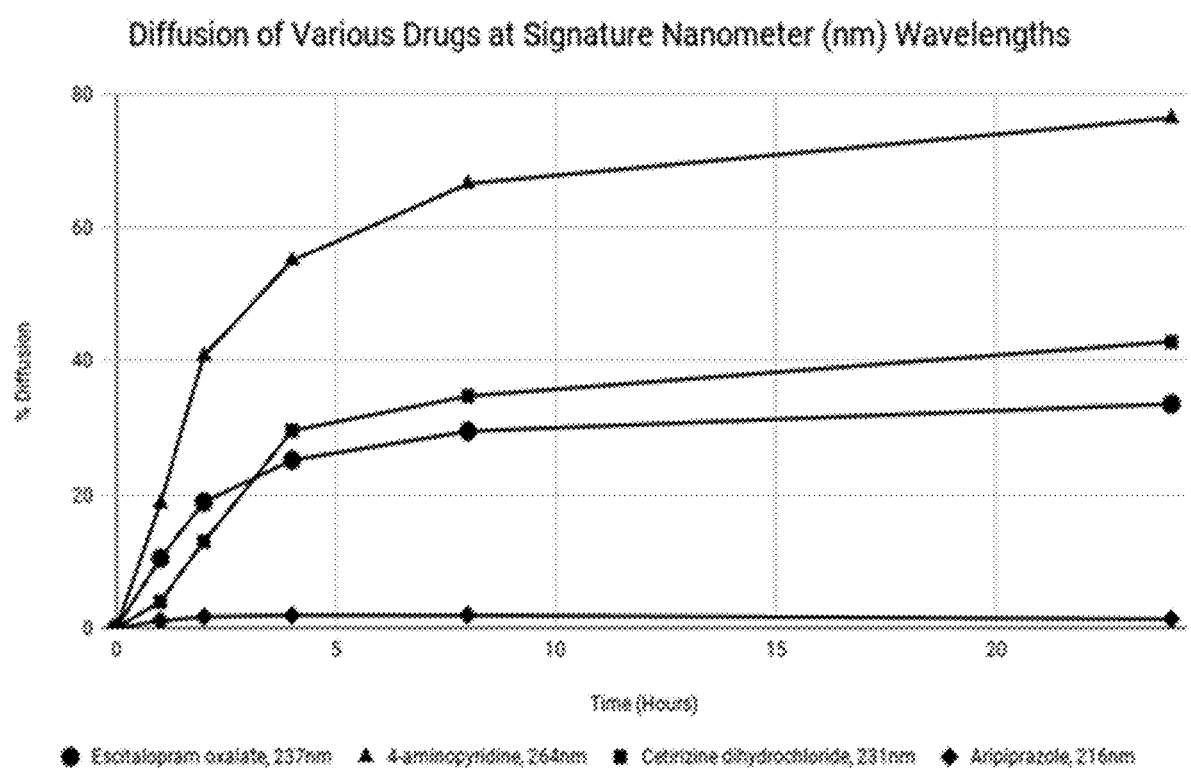
FIG. 3 shows in vitro diffusion of various drugs through a skin simulating membrane at air-water interface over time. ● Escitalopram oxalate; ▲ 4-aminopyridine; ■ cetirizine dihydrochloride; ♦ aripiprazole. Modified Franz Diffusion Cells were filled with 55 ml of phosphate buffer, and a skin simulating membrane was placed in each cell at air-water interface and secured with a holed cap. The cells were placed into a water bath and the temperature was equilibrated to 38° C. The drug-loaded patch was gently placed onto the membrane and pressed down lightly. At different time points, the drug solution was collected and replaced with fresh buffer, and ultraviolet (UV) absorbance was measured at 200-300 nm with clean quartz cuvettes, using standard curves to determine drug concentrations and cumulative drug release percentages over time.

The permeation or flux of several drugs transdermally delivered to the skin was measured in vitro as a function of time using an artificial skin simulating membrane attached to a Franz diffusion cell at air-water interface. Several measurements were taken to determine the flux of escitalopram oxalate, 4-aminopyridine, cetirizine dihydrochloride and aripiprazole over time. Modified Franz Diffusion Cells were filled with 55 ml of phosphate buffer, and a skin simulating membrane was placed in each cell at air-water interface and secured with a holed cap. The cells were placed into a water bath and the temperature was equilibrated to 38° C. The drug-loaded patch was gently placed onto the membrane and pressed down lightly. At different time points, the drug solution was collected and replaced with fresh buffer, and ultraviolet (UV) absorbance was measured at 200-300 nm with clean quartz cuvettes, using standard curves to determine drug concentrations and cumulative drug release percentages over time. FIG. 3 shows that the system is permeable to the diffusion of escitalopram oxalate, 4-aminopyridine, and cetirizine dihydrochloride, but it is impermeable to the diffusion of aripiprazole over time.

In view of these results, it was concluded that some drugs and small molecules may become "trapped" in the polymer matrix, and either precipitate out of the patch, or re-crystallize within the film, resulting in an effectively inert patch with reduced adhesive properties, and with no drug delivering abilities. Further experiments showed that small molecules that cannot permeate into skin and bloodstream through the patch matrix include caffeine, aripiprazole, theophylline, dyphilline, pentoxifyline, enprofylline, aminophylline, oxtriphylline, theobromine, propentofylline, xanthinol, doxofylline, pamabrom, lisofylline, ganciclovir, fenethylline, xanthine, uric acid, rolofylline, reproterol, cafedrine and theodrenaline.

Example 3: In Vivo Drug Diffusion Through the Transdermal Drug Delivery System

Figure 4:
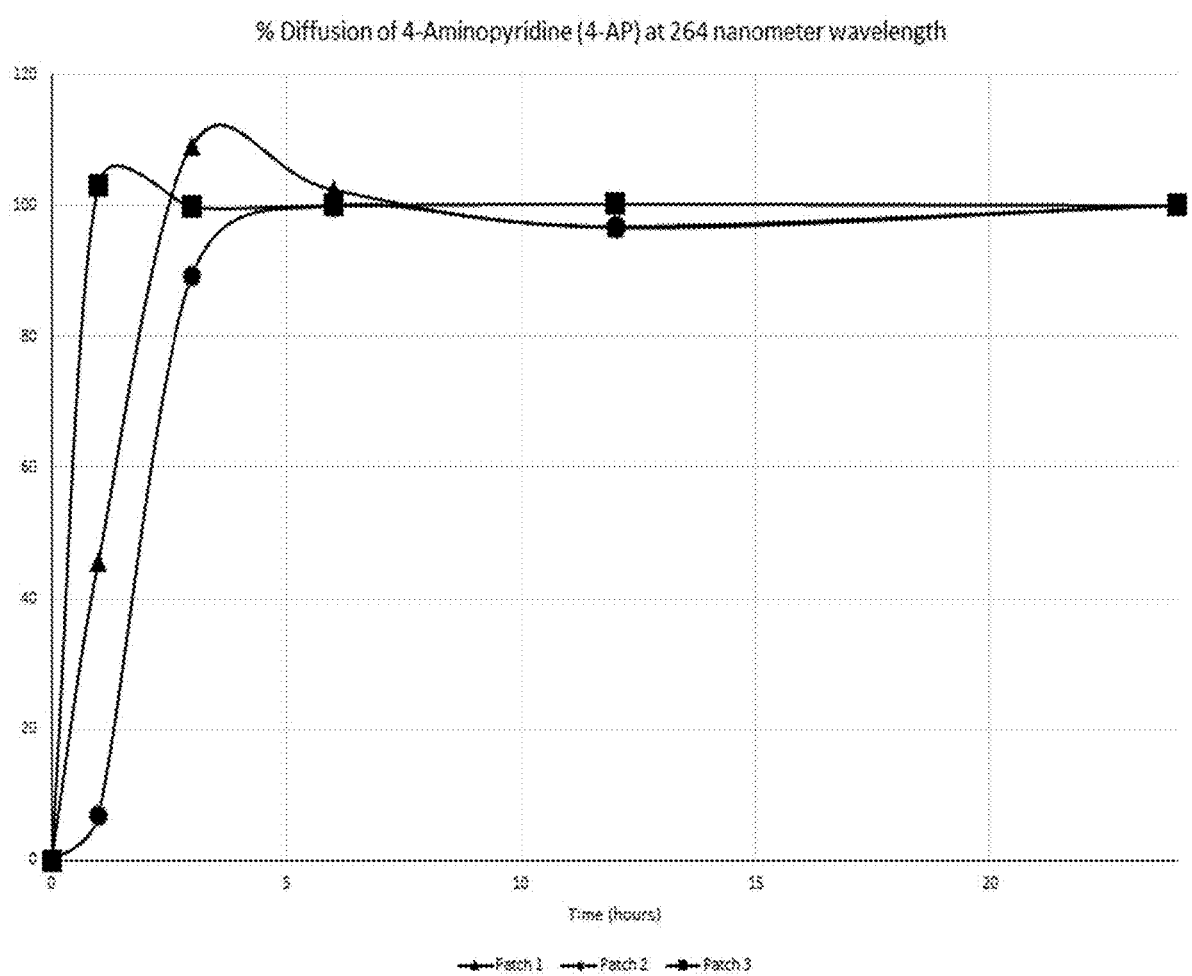
FIG. 4 shows the percentage diffusion of 4-aminopyridine through the transdermal drug delivery system provided herein over time. The patch in the transdermal drug delivery system consisted of 23% (w/w) glycerol, 16% (w/w) gum Arabic, 11% (w/w) medium molecular weight chitosan, and 48% (w/w) lactic acid. The patch was prepared by casting the liquid matrix gel upon a suitable Teflon backing layer and drying for 18 hours at 55° C. The resulting diffusion profiles were obtained by conducting the same experiment three times. The patch samples indicate the number of times that the same experiment was conducted.

The percentage diffusion of 4-aminopyridine through the transdermal drug delivery system provided herein was measured over time, using different patch compositions. FIG. 4 shows the percentage diffusion of 4-aminopyridine through a patch that consisted of 23% (w/w) glycerol, 16% (w/w) gum Arabic, 11% (w/w) medium molecular weight chitosan, and 48% (w/w) lactic acid. The patch was prepared by casting the liquid matrix gel upon a suitable Teflon backing layer and drying for 18 hours at 55° C. The resulting diffusion profiles indicate that the transdermal drug delivery system provided herein allows permeation and diffusion of 4-aminopyridine over time.

Figure 5:
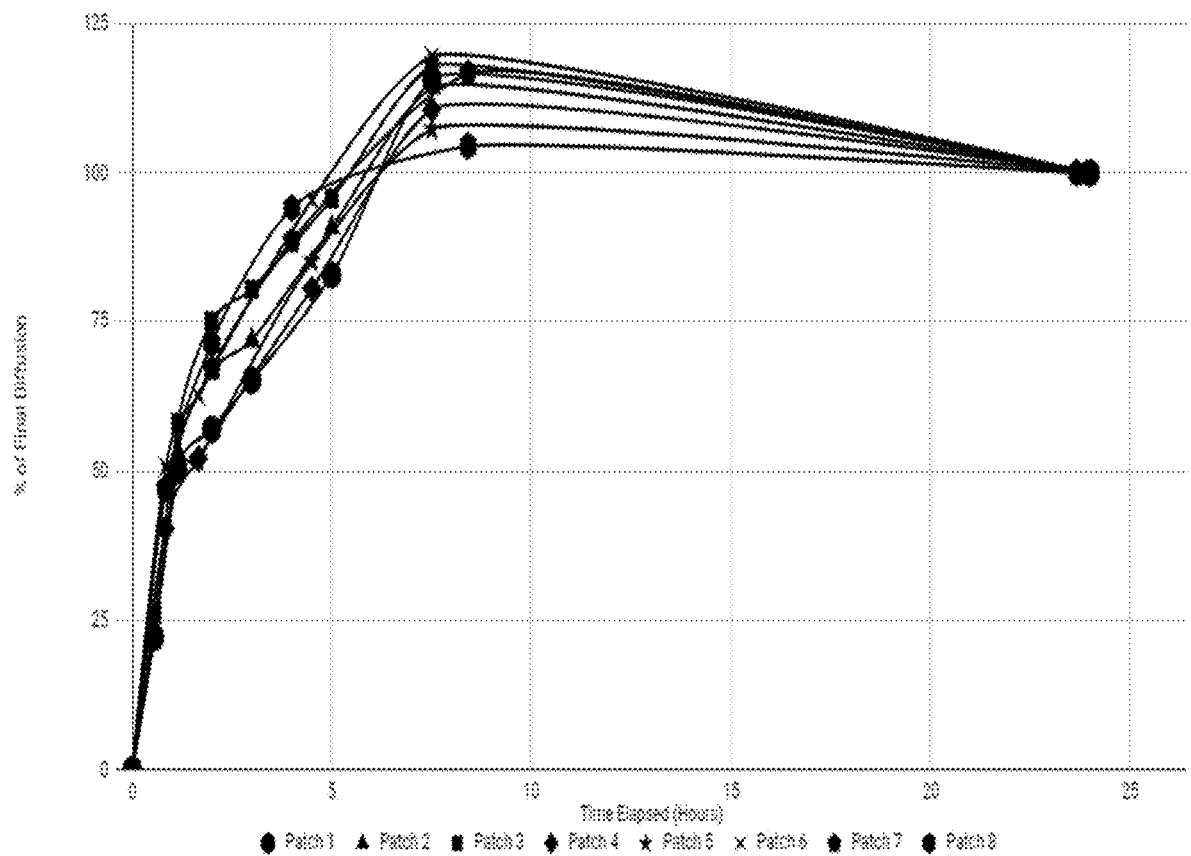
FIG. 5 shows the percentage diffusion of 4-aminopyridine through the transdermal drug delivery system provided herein over time. The patch in the transdermal drug delivery system consisted of 50% (w/w) glycerol, 14% (w/w) PVP, 18% (w/w) medium molecular weight chitosan, and 18% (w/w) lactic acid. The patch was prepared by casting the liquid matrix gel upon a suitable Teflon backing layer and drying for 3 hours at 80° C. The resulting diffusion profiles were obtained by conducting the same experiment eight times. The patch samples indicate the number of times that the same experiment was conducted.

FIG. 5 shows the percentage diffusion of 4-aminopyridine through a patch that consisted of 50% (w/w) glycerol, 14% (w/w) PVP, 18% (w/w) medium molecular weight chitosan, and 18% (w/w) lactic acid. The patch was prepared by casting the liquid matrix gel upon a suitable Teflon backing layer and drying for 3 hours at 80° C. The resulting diffusion profiles indicate that the transdermal drug delivery system provided herein allows permeation and diffusion of 4-aminopyridine over time.

Figure 6:
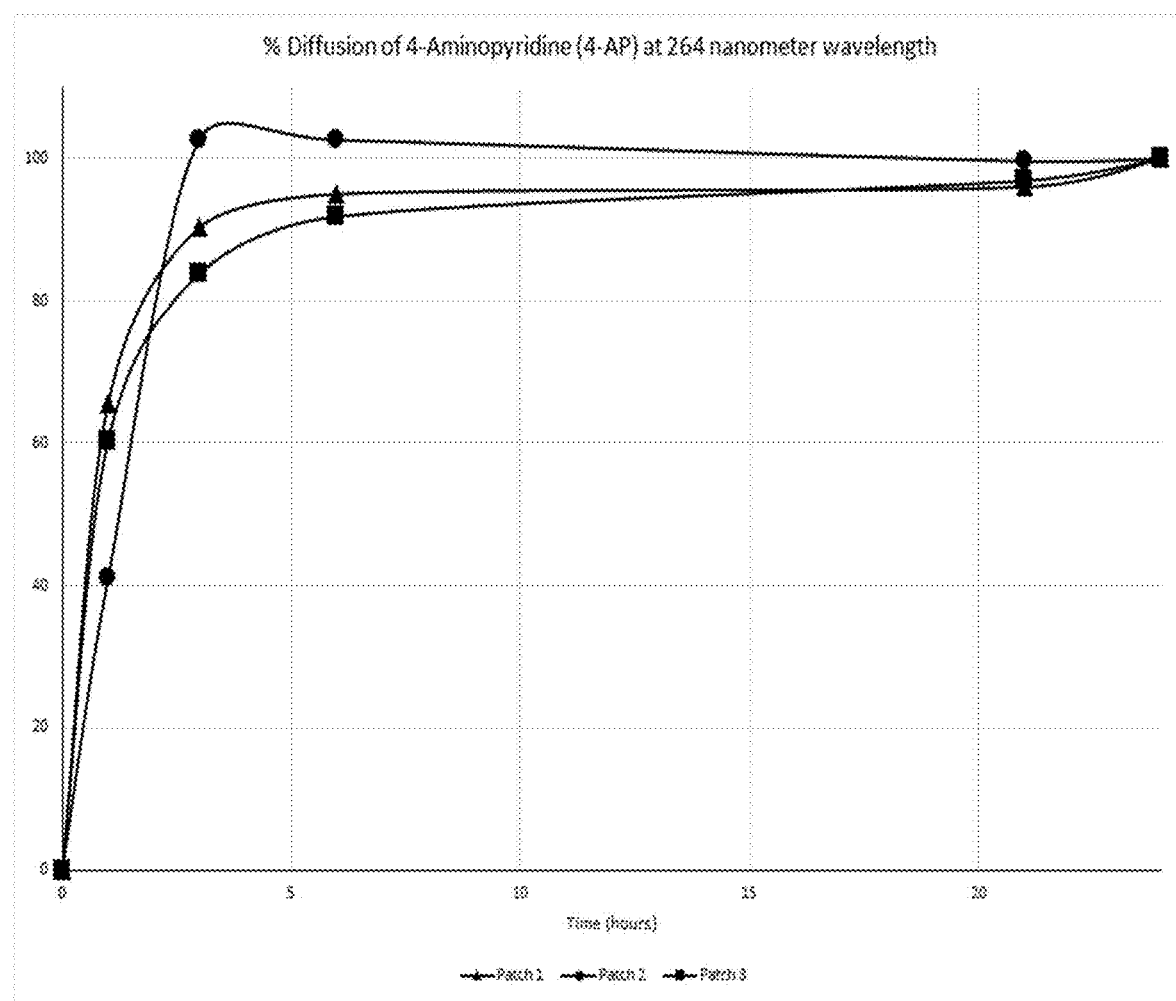
FIG. 6 shows the percentage diffusion of 4-aminopyridine through the transdermal drug delivery system provided herein over time. The patch in the transdermal drug delivery system consisted of 36% (w/w) glycerol, 15.3% PVP, 0.7% (w/w) gum Arabic, 9.5% (w/w) medium molecular weight chitosan, and 38.5% (w/w) lactic acid. The patch was prepared by casting the liquid matrix gel upon a suitable Teflon backing layer and drying for 5 hours at 80° C. The resulting diffusion profiles were obtained by conducting the same experiment three times. The patch samples indicate the number of times that the same experiment was conducted.
Figure 7:
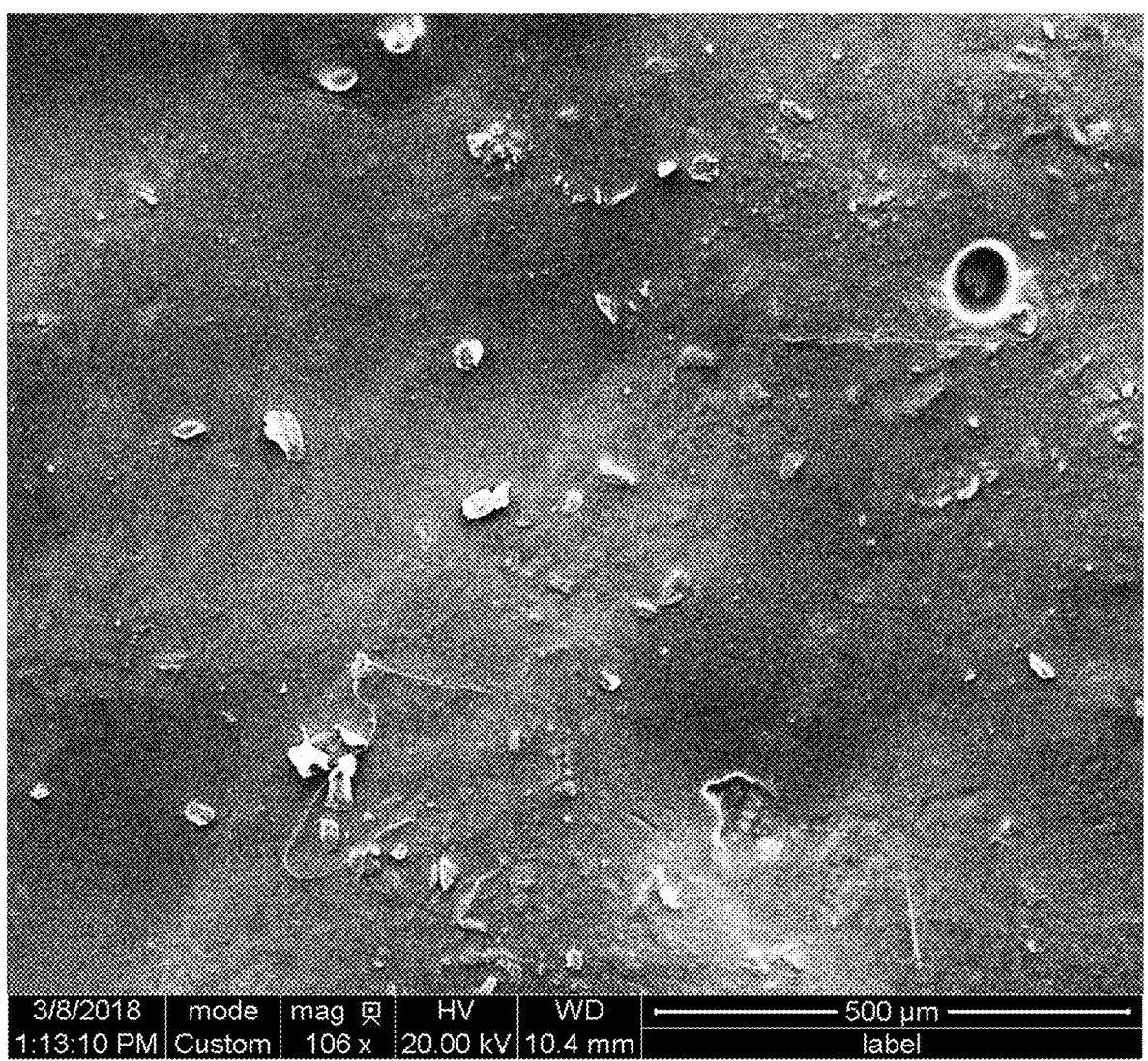
FIG. 7 provides a scanning electronic microscopy (SEM) image of the patch in the transdermal drug delivery system provided herein. A transdermal patch with desloratadine was formulated by first adding glycerol and lactic acid to a fixed volume of water while stirring the mixture at room temperature (25° C.). Chitosan and gum Arabic were next added gradually, to facilitate chitosan dissolution and reduce viscosity. PVP was then added to the matrix, and the mixture was stirred for 2-5 hours. Desloratadine was then added, and the mixture was stirred for 1-4 hours. The formulation was then casted onto an array of Teflon backings, and baked at 80° C. for 4-8 hours. The SEM image shows that the majority of the desloratadine, the active pharmaceutical ingredient (API) represented by a white powdery substance in the image, dissolved into the polymer matrix, represented by the dark background, while some desloratadine crystals were visible, indicating that the polymer has been saturated with the API.

FIG. 6 shows the percentage diffusion of 4-aminopyridine through a patch that consisted of 36% (w/w) glycerol, 15.3% PVP, 0.7% (w/w) gum Arabic, 9.5% (w/w) medium molecular weight chitosan, and 38.5% (w/w) lactic acid. The patch was prepared by casting the liquid matrix gel upon a suitable Teflon backing layer and drying for 5 hours at 80° C. The resulting diffusion profiles indicate that the transdermal drug delivery system provided herein allows permeation and diffusion of 4-aminopyridine over time.

Example 4: Treatment of Allergic Rhinitis by Transdermal Drug Delivery

A human subject suffering from severe symptoms of seasonal allergic rhinitis is treated with an antihistamine cocktail that comprises diphenhydramine, desloratidine, cetirizine, and loratadine. The antihistamine cocktail is administered transdermally to the skin of the human subject by applying the disclosed water- and sweat-resistant transdermal drug delivery system. The water- and sweat-resistant transdermal drug delivery system is maintained in contact with the skin of the subject for 24 hours. At the end of the treatment, the subject is free of symptoms associated with seasonal allergic rhinitis and presents no relapse even after renewed exposure to allergens.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

The invention claimed is:
1. A method of making a water- and sweat-resistant transdermal drug delivery system, wherein the method comprises:
creating a mixture by adding a film-forming agent and a plasticizer to water;
stirring the mixture at room temperature (25° C.);
gradually adding a bioadhesive polymer and a naturally occurring polysaccharide to the mixture;
stirring the mixture until the bioadhesive polymer is dissolved and viscosity is reduced;
adding a film-forming agent and a keratolytic agent to the mixture;
stirring the mixture for 2-5 hours until an even mixture is obtained;
obtaining a formulation by adding one or more active agents and stirring the mixture for 1-4 hours;
casting the formulation onto an array of backing layers; and
making a water-and sweat-resistant transdermal drug delivery system resulting from baking the backing layers at 80° C. for 4-8 hours, wherein one or more of backing layers further comprise at least one portion of an external skin surface patch comprising a hydrophilicity for maintaining adhesion on an external skin surface after the external skin surface transitions from a dry external skin surface to a wet external skin surface.

2. The method of claim 1, wherein the bioadhesive polymer is chitosan, hydroxypropylmethyl cellulose, hydroxyethyl cellulose, xanthan gum, guar gum, sodium alginate, or a combination thereof.

3. The method of claim 1, wherein the film-forming agent is polyvinyl alcohol, polyvinyl pyrrolidone, carrageenan, gelatin, dextrin, polyethylene oxide, guar gum, xanthan gum, or a combination thereof.

4. The method of claim 1, wherein the plasticizer is glycerol, sorbitol, polyethylene glycol, polypropylene glycol, polyethylene-propylene glycol, or a combination thereof.

5. The method of claim 1, wherein the naturally occurring polysaccharide is agar, alginate, chitin, glucomannan, gellan gum, gum guar, gum Arabic, locust beangum, pectin, xanthan, or a combination thereof.

6. The method of claim 1, wherein the keratolytic agent is urea, lactic acid, allantoin, benzoyl peroxide, salicyclic acid, or a combination thereof.

7. The method of claim 1, wherein the bioadhesive polymer is chitosan; the film-forming agent is polyvinylpyrrolidone; the plasticizer is glycerol; the naturally occurring polysaccharide is gum Arabic; and the keratolytic agent is lactic acid.

8. The method of claim 1, wherein the backing layers comprise Teflon, a metal foil, a metalized polyfoil, a composite foil, a film containing polyester, or a foam.

9. The method of claim 1, wherein the active agent is one or more of an antihistamine, a potassium channel blocker, an analgesic agent, an antidiabetic agent, a pain-relief agent, an antidepressant agent, an antipsychotic agent, an anti-Parkinsonian agent, a vasodilator, a diuretic, a calcium channel blocker, an anti-acne agent, an anti-aging agent, an antibiotic agent, an antifungal agent, an ACE inhibitor, a GERD medication, an anti-inflammatory agent, an opioid, an anti-asthma agent, a corticosteroid, a nicotinic cholinergic receptor agonist, an anti-oxidant agent, an antiprotozoal agent, an antipruritic agent, an antiviral agent, a chemotherapeutic agent, an immunomodulatory agent, a keratolytic agent, a retinoid, or a central nervous system stimulant.

10. The method of claim 1, wherein the active agent is one or more of Diphenhydramine, Desloratadine, Cetirizine, Loratadine, Trihexyphenidyl, Asenapine, Prostacyclin, Buspirone, Butorphanol, Captopril, Carbidopa, Albuterol, Naltrexone, Ivabradine, Dexamethasone, Phenylephrine, Fluocinolone acetonide, Dexlansoprazole, Furosemide, Isradipine, Venlafaxine, or Enalapril.

11. The method of claim 1, wherein the patch has a diameter between 1 and 8 cm in length, a surface area between 4 and 8 $cm^2$ and an onset of action within 15 minutes, and sustainably delivers one or more active agents for 8-24 hours; and wherein the patch has a peel rate of about 320 mm/min.

12. The method of claim 1, wherein the patch is occlusive to caffeine, aripiprazole, theophylline, dyphilline, pentoxifyline, enprofylline, aminophylline, oxtriphylline, theobromine, propentofylline, xanthinol, doxofylline, pamabrom, lisofylline, ganciclovir, fenethylline, xanthine, uric acid, rolofylline, reproterol, cafedrine and theodrenaline, or any combination thereof.

13. The method of claim 1, wherein 65% to 100% of the active agent diffuses into the skin of a mammal within 8 to 24 hours.

14. The method of claim 13, wherein the mammal is a human subject.

* * * * *